US008900175B2

(12) United States Patent
Pinto

(10) Patent No.: US 8,900,175 B2
(45) Date of Patent: Dec. 2, 2014

(54) DEVICE FOR MEDICAL USE FOR COLLECTING AND TRANSIT OF BLOOD, BLOOD DERIVATIVES AND/OR FILLER FLUIDS, AND AN EXTRACORPOREAL CIRCUIT COMPRISING THE DEVICE

(76) Inventor: Giovanni Pinto, San Nicola la Strada (IT)

( * ) Notice: Subject to any disclaimer, the term of this patent is extended or adjusted under 35 U.S.C. 154(b) by 0 days.

(21) Appl. No.: 13/543,773

(22) Filed: Jul. 6, 2012

(65) Prior Publication Data

US 2013/0012909 A1    Jan. 10, 2013

(30) Foreign Application Priority Data

Jul. 8, 2011   (IT) ............................... MI2011A1281
Jul. 8, 2011   (IT) ............................... MI2011A1282

(51) Int. Cl.
*A61M 37/00*   (2006.01)
*A61B 19/00*   (2006.01)
*A61M 1/00*    (2006.01)

(52) U.S. Cl.
CPC .................................. *A61M 1/0001* (2013.01)
USPC ........................... 604/6.15; 604/319; 604/403

(58) Field of Classification Search
USPC ........................................ 604/6.15, 319, 403
See application file for complete search history.

(56) References Cited

U.S. PATENT DOCUMENTS

| 3,845,765 A | 11/1974 | Ikeda |
| 3,866,608 A | 2/1975 | Reynolds et al. |
| 4,033,345 A * | 7/1977 | Sorenson et al. ............ 604/6.09 |
| 4,379,455 A | 4/1983 | Deaton |
| 4,959,062 A | 9/1990 | Gellman |
| 5,049,146 A * | 9/1991 | Bringham et al. ............ 604/6.09 |
| 5,062,835 A * | 11/1991 | Maitz et al. .................... 604/153 |
| 5,588,958 A | 12/1996 | Cunningham et al. |
| 6,123,519 A | 9/2000 | Kato et al. |
| 2004/0204693 A1 | 10/2004 | Anderson et al. |
| 2009/0275875 A1 | 11/2009 | Liebing et al. |

FOREIGN PATENT DOCUMENTS

| EP | 0870515 A1 | 10/1998 |
| EP | 0882440 A2 | 12/1998 |
| FR | 2639543 A1 | 6/1990 |
| FR | 2716806 A1 | 9/1995 |
| WO | 94/14045 A1 | 6/1994 |
| WO | 01/24846 A1 | 4/2001 |
| WO | 01/83003 A1 | 11/2001 |

OTHER PUBLICATIONS

Search Report for Italian Patent Application No. MI2011A001281, dated Apr. 2, 2012.

* cited by examiner

*Primary Examiner* — Leslie Deak
(74) *Attorney, Agent, or Firm* — Oliff PLC

(57) ABSTRACT

A collecting device for fluids for medical use may include a rigid container internally defining a first chamber having a fixed volume, an auxiliary container having a deformable portion defining internally thereof a second chamber having a variable volume as a function of a deformable portion thereof, a passage able to set the first and the second chamber in fluid communication, an inlet port connected to at least one of the containers, and an outlet port connected to at least one of the containers, as well as a bypass line for bypassing the device.

31 Claims, 14 Drawing Sheets

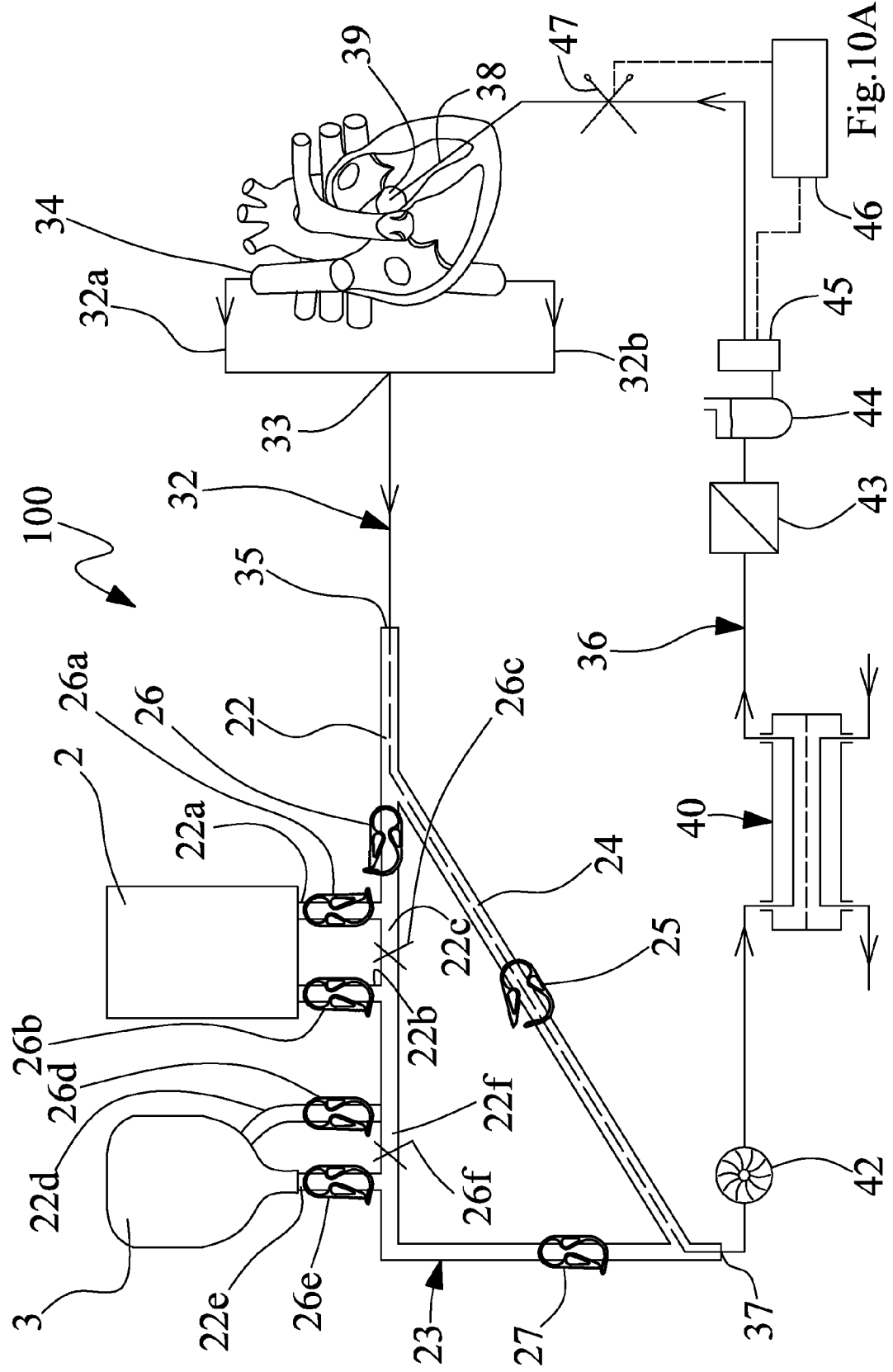

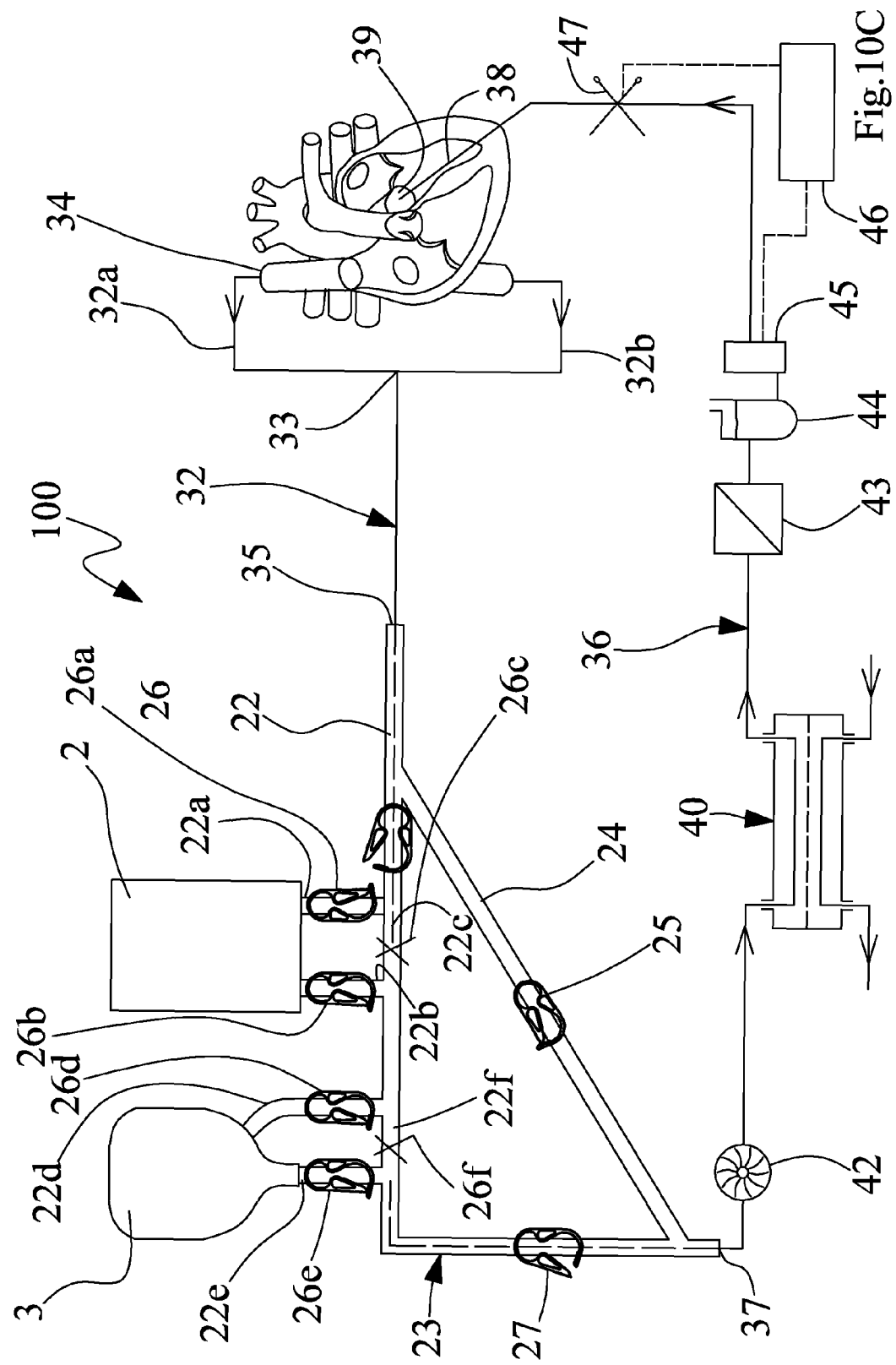

DEVICE FOR MEDICAL USE FOR COLLECTING AND TRANSIT OF BLOOD, BLOOD DERIVATIVES AND/OR FILLER FLUIDS, AND AN EXTRACORPOREAL CIRCUIT COMPRISING THE DEVICE

CROSS-REFERENCE TO RELATED APPLICATION

This application claims the benefit of priority of Italian Patent Application No. MI2011A001281, filed Jul. 8, 2011, and Italian Patent Application No. MI2011A001282, filed Jul. 8, 2011, pursuant to 35 U.S.C. 119(a)-(d), the disclosures of which are incorporated herein by reference.

TECHNICAL FIELD

The invention relates to a collecting device, or reservoir, for medical use, for collecting and transiting blood and/or blood derivatives and/or filler fluids and to an extracorporeal circuit comprising the reservoir.

In particular, the invention is applicable in an extracorporeal blood circulation, for example during surgical treatment when assistance to or replacement of heart and/or lung function is to be provided.

In these situations, an extracorporeal circuit is used for removing blood from a patient subjected to treatment, carrying it towards a reservoir for collection of fluid and then returning the blood, after a specific treatment, to the patient.

The device or reservoir of the invention can be used as an independent component internally of a system for extracorporeal circulation comprising for example a blood collecting line, a pump, a heat exchanger, an oxygenating section, a blood return line to the patient, or it can be an integral part of a membrane oxygenator integrating, in a single piece, the collecting device or reservoir according to the invention and possibly a heat exchanger.

BACKGROUND OF THE INVENTION

Extracorporeal circuits are known of a type referred to as "open", which comprise a venous branch for blood collection, at least a rigid reservoir superiorly connected to the atmosphere and at least a return line of the treated blood (for example filtered and/or oxygenated) to the patient.

This first type of circuit using a rigid reservoir exhibits the drawback of typically offering a large contact surface between the free surface of the blood in the reservoir and the air, with a consequent possibility of activation of the air-blood contact and therefore the development of reactive phenomena on the part of the patient, which might initiate inflammation, activation of complement and coagulation, certainly undesired during extracorporeal circulation.

Together with the above-described "open" systems using a rigid reservoir, extracorporeal circulation system of the "closed" type are widely known.

The closed types comprise a venous line of the patient's blood, at least a bag able to contain a predetermined blood quantity, and a return line of the treated blood to the patient.

Thanks to the use of closed bags, there is the advantage of reducing to a minimum, and almost eliminating, the contact between the air and blood.

The disadvantages of the closed type systems are primarily connected to the greater operating complexity thereof due to the presence of an additional module (bag) connected by means of a line to a rigid reservoir containing the filtered blood; secondly, any air bubbles that might be present in the venous line are not automatically eliminated as the bag is a closed reservoir and therefore in order to separate and liberate externally any air trapped in the bag, it is necessary for the bag to be provided in a high part thereof with a breather valve.

Should the venous line be carrying numerous air bubbles, there is further the risk that the deformable bags might accumulate an excessive quantity of air.

In this case the circulation pump typically present, downstream of the bag, might aspirate one or more air bubbles present in the bag itself, sending them to the patient, with very grave consequences for the patient.

A system reducing the drawback constituted by air bubbles that might be present in the venous line includes using defoaming membranes, and maintaining an adequate level of blood in the bag, as well as placing the bag in contact with the air through a breather line.

Definitively, the known systems exhibit either the drawback of exhibiting a relevant contact zone between the blood and the air or a certain degree of inefficiency in the separation and consequent sure evacuation of the air bubble that might have collected in the venous line of blood aspiration from the patient.

Apart from the above-described drawbacks, the systems of known type exhibit a poor functionality and poor ability to adapt to various types of treatment, as the operator each time has to use a new circuit such as to respond to treatment requirements or treatments that time by time are to be applied.

In this situation, an aim of the invention is to obviate one or more of the drawbacks and/or limitations described herein above.

In particular, one of the aims of the invention is to provide a reservoir and an extracorporeal circuit using the reservoir which are able to provide greater flexibility with respect to the solutions of known type.

A further aim of the invention is to provide a technical solution which enables minimizing, as far as possible, contact between blood or other blood derivatives and the air.

A further aim is to provide a technical solution able to allow accumulation of relatively important quantities of blood externally of the human body during operating stages which for example comprise evacuation from the human body of significant quantities of blood or another biological fluid.

A further aim of the invention is to provide a technical solution which enables efficient filtering of the aspirated blood coming from the operating field.

A further auxiliary aim is to provide a solution in which the venous blood of the patient directly reaches the collecting device while receiving a suitable de-foaming action.

A further auxiliary aim of the invention is to make available a technical solution able suitably to treat, for example by oxygenation, the blood to be returned to the patient subjected to treatment.

One or more of the above aims, which will better emerge during the course of the following description, is substantially attained by a collecting device and an extracorporeal circuit using the device, according to one or more of the accompanying claim.

SUMMARY

A 1st aspect relates to a collecting device of biological fluids for medical use, comprising a container comprising: a rigid container internally defining at least a first chamber having a fixed volume; and an auxiliary container having at least a deformable portion internally defining a second chamber having a variable volume according to a position of the deformable portion; at least an inlet port connected with at least one of the containers; and at least an outlet port connected with at least one of the containers. A passage, which may be provided with a valve for opening and closing the fluid flow, sets the first and the second chamber in fluid communication.

In a 2nd aspect according to the 1st aspect, the rigid container exhibits a box conformation having a bottom wall, a lateral wall emerging from the bottom wall and a closing portion located at a top of the lateral wall, the walls defining the volume of the first chamber.

In a 3rd aspect according to the preceding aspect the device comprises at least one ventilation line predisposed for connecting the first chamber and the external environment.

In a 4th aspect according to any one of the preceding aspects the auxiliary container comprises at least one deformable wall peripherally constrained to the lateral wall of the rigid container.

In a 5th aspect according to aspects 3 or 4, the device comprises at least a ventilation line, predisposed such as to create a connection between the first chamber and the external environment and selectively openable-closable by means of an intercept member located on the ventilation line.

In a 6th aspect according to any one of the preceding aspects, the rigid container and the auxiliary container are mutually flanked.

In a 7th aspect according to aspects from 2 to 6, a portion of the lateral wall of the rigid container acts as a separating wall between the first and the second chamber and constitutes a portion of wall which is in common between the rigid container and the auxiliary container.

In an 8th aspect according to aspects from 2 to 7, a part emerges from a portion of lateral wall of the rigid container, with reference to an operating configuration in which the lateral wall extends from below in an upwards direction, the part developing inferiorly with respect to the first chamber and in prolongation with respect to the lateral wall.

In a 9th aspect according to the preceding aspect the auxiliary container comprises a rigid wall formed by a portion of the lateral wall of the rigid container and by the inferiorly-extending part with respect to the first chamber.

In a 10th aspect according to claim 8 or 9, the auxiliary container comprises a flexible wall perimetrally and sealedly fixed on the rigid wall of the auxiliary container.

In an 11th aspect according to the preceding aspect, the flexible wall is fixed to the rigid wall by means of welding or gluing.

In a 12th aspect according to any one of aspects from 8 to 11, the part extending inferiorly of the first chamber exhibits an arched conformation having a concavity facing towards an inside of the second chamber.

In a 13th aspect according to any one of the preceding aspects the passage which sets the first and the second chamber in fluid communication is located at the bottom of the first chamber.

In a 14th aspect according to any one of the preceding aspects, the device comprises at least a fluid intercept member activatable manually from outside by means of a tap or commandable by means of an actuator organ and operating at the passage which sets the first and the second chamber in fluid communication.

In a 15th aspect according to the preceding aspect, the fluid intercept member is displaceable between a first operating position in which a fluid passage is enabled between the first and the second chamber and a second operating condition in which the fluid passage between the first chamber and the second chamber is prevented.

In a 16th aspect according to any one of the preceding aspects, the inlet port of the collecting device is situated such as to enable inlet directly into the second chamber. Also, the outlet port of the collecting device may be situated such as to enable outlet directly from the second chamber. In the case where both the inlet and the outlet port are directly connected to the second chamber, it is the fluid present in the second chamber which is primarily used. The first chamber is in this case connected to the outlet of the collecting device only via said passage setting the first and second chambers in fluid communication.

In a 17th aspect according to any one of the preceding aspects from 8 to 16, the inlet port is located at the rigid part extending inferiorly to the first chamber.

In an 18th aspect according to any one of the preceding aspects the outlet port is located at the lower position, with reference to an operating condition of the device, than the second chamber.

In a 19th aspect according to any one of the preceding aspects from 8 to 18, the outlet port is located at the vertically lowest zone of the rigid part emerging inferiorly to the first chamber.

In a 20th aspect according to any one of the preceding aspects, the inlet and/or outlet ports are located, with reference to an operating condition of the device, at a lower height with respect to the passage which sets the first and the second chamber in fluid communication.

In a 21st aspect according to any one of the preceding aspects from 14 to 20, the fluid intercept member comprises a wall element which is substantially cylindrical and rotatably engaged internally of the passage, and which has at an axial end thereof a fluid passage opening set in communication with the second chamber and further having a fluid passage opening realized at a lateral wall of the cylindrical surface; following an angular rotation of the fluid intercept member, the opening located on the cylindrical wall being displaceable between a condition in which the opening opens towards the first chamber and sets towards the first chamber in fluid communication with the second chamber, and a second angularly offset position with respect to the first position in which the opening located on the cylindrical lateral wall is closed by a corresponding part of the passage, in this way preventing fluid communication between the first and the second chamber.

In a 22nd aspect according to any one of the preceding aspects, the device comprises at least a filter element located at the first chamber and having an access side for receiving fluid to be filtered coming from one or more connectors for the aspirating lines, and an outlet side able to supply filtered fluid towards the bottom wall of the first chamber.

In a 23rd aspect according to any one of the preceding aspects the device comprises a supply channel fixed to the inlet port, a discharge channel fixed to the outlet port, and a bypass channel which exhibits a first end connected to the supply channel and a second end connected to the discharge channel for bypassing the fluid collecting device.

In a 24th aspect according to the preceding aspect the device comprises a fluid intercept member on the bypass channel, an intercept member, for example a clamp, operating on the supply channel in a zone comprised between the inlet port and the ends of the bypass channel, and an intercept member operating on the discharge channel in a zone comprised the outlet port and another end of the bypass channel.

In a 25th aspect according to the preceding aspect each intercept member arranged on the supply channel, on the discharge channel and on the bypass channel comprises at least one selected from: an elastic clamp manually activatable between an open position and a closed position in which it clamps the respective portion of tube on which the clamp operates, a fluid intercept valve manually activatable by a user, a fluid intercept valve activatable by an actuator organ commanded by a control unit.

In a 26th aspect according to any one of the preceding aspects the device comprises a connector element, for example a Luer connector, located on a terminal part of the supply channel opposite the inlet port; and a connector element, for example a Luer connector, located on the discharge channel opposite the outlet port, the connectors being configured for enabling engagement and disengagement of the collecting device with respect to a respective line of an extracorporeal circuit, the Luer connectors exhibiting, for example, following dimensions: ½" for a device for adult use, ⅜" for pediatric use and ¼" for neonatal use.

In a 27th aspect according to any one of the preceding aspects the device comprises at least an ampoule operatively connected upstream of the inlet port and comprising internally thereof at least a hydrophilic membrane for allowing passage of fluid from an upstream section of the ampoule towards a downstream section thereof, reducing the air passage, the membrane being arranged internally of the ampoule separating the ampoule into an upstream semichamber and a downstream semichamber, a gas evacuation passage being provided at the upstream semichamber.

In a 28th aspect according to any one of the preceding aspects from 8 to 27, the bottom wall of the first chamber is inclined downwards proceeding nearingly to the second chamber, such that outflow of fluid through the connecting passage from the first to the second chamber is facilitated.

A 29th aspect relates to an extracorporeal circuit for blood treatment comprising: at least a removal line of the blood having a first end that is connectable to at least an access to the patient and at least a second end placed in fluid communication with the inlet port to the collecting device; at least a return line of the blood having a first end connected to the outlet port of the collecting device and at least a second end connectable to an access of the cardiovascular system of the patient; and at least a collecting device interposed between the removal line and the return line, the collecting device being of a type as in any one of the preceding aspects.

In a 30th aspect according to the preceding aspect the circuit comprises at least a blood oxygenating unit located downstream of the collecting device, at the blood return line to the patient.

In a 31st aspect according to aspects 29 or 30, the circuit comprises a pump at the return line, optionally at a tract of the return line comprised, optionally at a tract of the return line comprised between the collecting device and the oxygenator.

In a 32nd aspect according to the preceding aspect the pump comprises a centrifugal pump or a peristaltic pump, for example a roller-type peristaltic pump.

In 33rd aspect according to any one of aspects from 29 to 32, the circuit comprises a filter located on the return line downstream of the oxygenator.

In a 34th aspect according to any one of aspects from 29 to 33, the circuit comprises an air bubble separator, located at the return line.

In a 35th aspect according to any one of aspects from 29 to 34, the circuit comprises an air-bubble detector organ arranged on the return line at or downstream of the air bubble separator.

In a 36th aspect a use procedure is comprises of a device of any one of aspects from 2 to 28 in an extracorporeal circuit according to any one of aspects from 29 to 35, the use procedure including a bypass mode in which the device is excluded from the extracorporeal circuit as the intercept members on the supply channel and discharge channel are closed while the intercept member on the bypass channel is open; in this mode the blood can be for example oxygenated, without however using any fluid present in one or the other of the two containers which are thus excluded from the extracorporeal circuit.

A 37th aspect comprises use of a device as in any one of aspects from 1 to 28, in an extracorporeal circuit according to any one of aspects from 29 to 35, the use procedure including a mode in which the device is active and the intercept member is closed; in this case the intercept members on the supply channel and the discharge channel are open while the organ on the bypass channel is closed; in this operating mode, the extracorporeal circuit exclusively uses the volume of the deformable chamber (because the passage connecting the first and the second chamber is kept closed), in effect operating as a closed circuit substantially without or with only a minimum contact with air; the fluid removed from the patient proceeds in the venous branch, reaches the container though the inlet port, exits from the outlet port, reaches the pump, crosses the oxygenator (if present) and any other units then to return to the patient through the second end of the return line; at the emptying of the container where the blood accumulates, the deformable portion of the container rests on the internal surface of the part acting to close the outlet port; in this regard note that a tab or other grip element can be provided, emerging from the deformable portion, which can be used to facilitate the separation of the deformable portion from the part.

A 38th aspect comprises use of a device as in any one of aspects from 1 to 28, the use procedure comprising a mode in which the passage connecting the first and second chambers is open: in this case too the organs on the supply channel and discharge channel are open while the organ on the bypass channel is closed; in this operating mode, the extracorporeal circuit uses both the volume of the deformable container and the volume of the rigid container, in effect operating as an open system with a high blood or other fluid storage capacity. Note that in each case the rigid container can receive the blood coming from the operating field and therefore comprising clots, bone and tissue fragments, fat and other matter which can be adequately filtered by the filter present in the rigid container; in this case too the fluid collected from the patient proceeds in the venous branch, reaches the container and also the other container, as the two containers are connected by the passage. The blood then exits from the port, reaches the pump, crosses the oxygenator and any other units then to return to the patient through the second end of the return line; as mentioned, the container can also receive blood or another fluid through connectors for the aspirating, infusion or arterial-venous recycling lines. In this operating mode, however, the fluid level in the containers is practically equal, as the two containers are connected. Obviously in case of need the operator can disconnect the communication between the two containers simply by acting on the intercept member operating on the passage.

In a 39th aspect a biological collecting device for medical use is comprised, comprising: at least a container selected from a group comprising: at least a container selected from a group comprising a rigid container internally defining at least a first chamber having a fixed volume and an auxiliary container having at least a deformable portion internally defining a second chamber having a variable volume according to a position of the deformable portion, at least an inlet port connected with at least one of the containers, at least an outlet port connected with at least one of the containers, a supply channel connected with the inlet portion, a discharge channel connected with the outlet port, a bypass channel exhibiting a first end connected to the supply channel and a second end connected to the discharge channel such as to bypass the fluid collector device, a fluid intercept member operating on the bypass channel and at least one from between a fluid intercept member operating on the supply channel and an intercept member operating on the discharge channel.

In a 40th aspect according to the preceding aspect, the device comprises a rigid container internally defining at least a first chamber having a fixed volume and an auxiliary container having at least a deformable portion internally defining a second chamber having a variable volume according to a position of the deformable portion, optionally wherein the deformable container comprises a bag.

In a 41st aspect according to aspects 39 or 40, the device comprises at least a passage able to set the first and the second chamber in fluid communication.

In a 42nd aspect according to any one of the preceding aspects each container comprises a respective inlet port and a respective outlet port, or wherein only the auxiliary container comprises both the inlet port and the outlet port. In the case where both the inlet and the outlet port are directly connected to the second chamber, it is the fluid present in the second chamber which is primarily used. The first chamber is in this case connected to the outlet of the collecting device only via said passage setting the first and second chambers in fluid communication.

In a 43rd aspect according to any one of the preceding aspects from 40 to 42, the rigid container exhibits a box conformation having at least a bottom wall, at least a lateral wall emerging from the bottom wall and at least a closing portion located at a top of the lateral wall, the walls defining the volume of the first chamber.

In a 44th aspect according to any one of the preceding aspects the device comprises at least a ventilation line, predisposed such as to create a connection between the first chamber and the external environment.

In a 45th aspect according to any one of the preceding aspects from 39 to 44, the auxiliary container is defined by at least a deformable portion that is perimetrally constrained to at least a corresponding portion of the lateral wall of the rigid container.

In a 46th aspect according to any one of aspects from 39 to 45, the rigid container and the auxiliary container are mutually flanked.

In a 47th aspect according to any one of aspects from 43 to 46, a portion of the lateral wall of the rigid container separates the first and the second chamber and constitutes a portion of wall in common between the rigid and auxiliary containers, or the container comprises a respective bag solidly connected with the rigid container.

In a 48th aspect according to any one of aspects from 43 to 47, a portion of lateral wall of the rigid container, with reference to an operating configuration in which the lateral wall extends from below in an upwards direction, the part developing inferiorly with respect to the first chamber and in prolongation with respect to the lateral wall.

In a 49th aspect according to the preceding aspect, the auxiliary container comprises a rigid wall formed by a portion of the lateral wall of the rigid container and by the inferiorly-extending part, and a flexible wall perimetrally and sealedly fixed to the rigid wall of the auxiliary container.

In a 50th aspect according to aspects 48 and 49, the rigid part extending inferiorly of the first chamber exhibits an arched conformation having a concavity facing towards an inside of the second chamber.

In a 51st aspect according to any one of aspects from 39 to 50, the passage which sets the first and the second chambers in fluid communication is located at the bottom of the first chamber.

In a 52nd aspect according to any one of aspects from 39 to 51, the bottom wall of the first chamber is inclined downwards proceeding nearingly to the second chamber, such that outflow of fluid through the connecting passage from the first to the second chamber is facilitated.

In a 53rd aspect according to any one of aspects from 39 to 52, the device comprises a fluid intercept member that is manually activatable from outside by means of a tap or commandable by an actuator organ and operating at the passage setting the first and the second chamber in fluid communication.

In a 54th aspect according to the preceding aspect, the fluid intercept member is displaceable between a first operating position in which a fluid passage is enabled between the first and the second chamber and a second operating condition in which the fluid passage between the first chamber and the second chamber is prevented.

In a 55th aspect according to aspects 53 and 54, the fluid intercept member comprises a wall element which is substantially cylindrical and rotatably engaged internally of the passage, and which has at an axial end thereof a fluid passage opening set in communication with the first and/or second chamber and further having a fluid passage opening made at a lateral wall of the cylindrical surface; following an angular rotation of the fluid intercept member, the opening located on the cylindrical wall being displaceable between a condition in which the opening opens towards the first chamber and sets the first chamber in fluid communication with the second chamber, and a second angularly offset position with respect to the first position in which the opening located on the cylindrical lateral wall is closed by a corresponding part of the passage, in this way preventing fluid communication between the first and the second chamber.

In a 56th aspect according to any one of aspects 48 to 55, the inlet port is localized at the rigid part extending inferiorly of the first chamber and the outlet port is localized at the lower position, with reference to an operating condition of the device, of the second chamber.

In a 57th aspect according to any one of aspects from 48 to 56, the outlet port is localized at the vertically lowest zone of the rigid part.

In a 58th aspect according to any one of aspects from 39 to 57, the inlet port and/or the outlet port are localized, with reference to an operating condition of the device, at a lower height with respect to the passage placing the first chamber in fluid communication with the second chamber.

In a 59th aspect according to any one of aspects from 39 to 58, the rigid container comprises at least a filter element located at the first chamber and having an access side for receiving fluid to be filtered coming from connectors for the aspirating lines, and an outlet side able to supply filtered fluid towards the bottom wall of the first chamber.

In a 60th aspect according to any one of aspects from 39 to 59, the supply channel comprises at least a first channel which sets the supply channel in fluid communication with the inlet port of the rigid container, and at least a second channel which sets the supply channel in fluid communication with at least the outlet port of the rigid container.

In a 61st aspect according to any one of aspects from 39 to 60, the supply channel comprises at least a third channel which sets the supply channel in fluid communication with at least the inlet port of the auxiliary channel, and at least a fourth channel which sets the supply channel in fluid communication with at least the outlet port of the auxiliary container.

In a 62nd aspect according to the preceding aspect, an intercept member operates on the first channel, on the second channel and/or on a tract of the supply channel which connects the first channel with the second channel; and/or wherein an intercept member operates on the third channel, on the fourth channel and/or on a tract of the supply channel which connects the third channel with the fourth channel.

In a 63rd aspect according to any one of aspects from 60 to 62, the first end of the bypass channel is connected upstream of the intercept member applied on the first channel.

In a 64th aspect according to any one of aspects from 60 to 63, the second end of the bypass channel is connected downstream of the intercept member applied on the second channel.

In a 65th aspect according to any one of aspects from 60 to 64, the second end of the bypass channel is connected downstream of the fourth channel.

A 66th aspect relates to an extracorporeal circuit for blood treatment, comprising: at least a removal line of the blood having a first end that is connectable to at least an access to the patient and at least a second end placed in fluid communication with at least an inlet port to the collecting device; at least a return line of the blood having a first end connected to the outlet port of the collecting device and at least a second end connectable to an access to the cardiovascular system of the patient; and at least a collecting device interposed between the removal line and the return line, the collecting device being of a type as in any one of the preceding aspects from 39 to 65.

In a 67th aspect according to the preceding aspect, the circuit comprises at least a blood oxygenating unit located downstream of the collecting device, at the blood return line to the patient.

In a 68th aspect according to the preceding aspect, the oxygenation device comprises a semipermeable membrane separating the oxygenation device into a first chamber in which the blood coming from the collecting device flows and a second chamber separated by the membrane from the first chamber into which an oxygenating fluid flows towards the blood.

In a 69th aspect according to any one of aspects from 66 to 68, a pump is comprised at the return line.

In a 70th aspect according to the preceding aspect, the pump is arranged at a tract of the return line comprised between the collecting device and the oxygenator.

A 71st aspect according to any one of aspects 69 or 70 comprises a centrifuge pump or a peristaltic pump, for example having rollers.

In a 72nd aspect according to any one of aspects from 66 to 71, the circuit comprises a filter located on the return line downstream of the oxygenator.

In a 73rd aspect according to any one of aspects from 66 to 72, the circuit comprises an air-bubble separator, also located at the return line.

In a 74th aspect according to any one of aspects from 66 to 73, the circuit comprises a detector organ of air bubbles present on the return line at or downstream of the air bubble separator.

A 75th aspect relates to a use procedure of a device according to any one of aspects from 39 to 65 in an extracorporeal circuit according to any one of aspects from 66 to 74, the use procedure comprising a bypass mode, wherein the device is excluded from the extracorporeal circuit as the organs arranged on the supply channel and/or on the discharge channel are closed while the intercept member arranged on the bypass channel is open: in this mode the blood can be for example oxygenated, without however the use of any fluid present in one or the other of the two containers which are thus excluded from the circuit.

A 76th aspect relates to a use procedure of a device of any one of aspects from 39 to 65 in an extracorporeal circuit according to any one of aspects from 66 to 74, the use procedure comprising a mode with the device active and use of the auxiliary container only: in this case at least a part of the intercept members arranged on the supply channel are open while the intercept member arranged on bypass channel is closed; in this operating mode, the extracorporeal circuit exclusively exploits the volume of the auxiliary container operating in fact as a closed circuit substantially without or with minimum contact with the air; the fluid removed from the patient proceeds in the venous branch, reaches the container via the inlet port in communication with the third channel, exits from the port in fluid communication with the fourth channel, reaches the pump, crosses the oxygenator and any other units, and then returns to the patient through the second end of the return line.

A 77th aspect relates to a use procedure of a device according to any one of aspects from 39 to 65 in an extracorporeal circuit according to any one of aspects from 66 to 74, the use procedure comprising a mode having the device active, and use of the rigid container: in this case the intercept members arranged on the supply channel are at least partly open while the intercept member arranged on the bypass channel is closed; in this operating mode, the extracorporeal circuit exclusively exploits the volume of the container operating as an open circuit; the fluid removed from the patient proceeds in the venous branch, reaches the container through the inlet port in communication with the first channel, exits from the portion in fluid communication with the second channel, reaches the pump, crosses the oxygenator and, possibly, other units, then to return into the patient through the second end of the return line.

A 78th aspect relates to a use procedure of a device according to any one of aspects from 39 to 65 in an extracorporeal circuit according to any one of aspects from 66 to 74, the use procedure comprising a mode with the device active and use of both the rigid container and the auxiliary container: in this case too at least one of the intercept members arranged on the supply channel is open while the intercept member arranged on the bypass channel is closed; the device is provided with the passage, and it is possible to close the second and the third channels and the channels connecting the first channel with the second channel and the channel connecting the third channel and the fourth channel, while the first and the fourth channels are kept open, as well as in the intercept member arranged on the passage connecting the two containers; in this operating mode, the extracorporeal circuit exploits the volume of the deformable container and the volume of the rigid container by operating in effect as a hybrid circuit having a high blood or other fluid storage capacity—note that in this case the rigid container can receive, from the opening, blood arriving from the operating field and as such comprising clots, blood fragments and more besides which can be adequately filtered by the filter present in the rigid container; in this case too the fluid removed from the patient proceeds in the venous branch, reaches the container and also the auxiliary container, as the two containers are connected. The blood exits the port of the auxiliary container, reaches the pump, crosses the oxygenator and any other units present, then to return to the patient through the second end of the return line; as mentioned, the container can be predisposed to receive also blood or another fluid through the opening. In this operating mode, however, the level of fluid in the containers is practically equal, as the two containers are connected.

The collection reservoir can be made in differing dimensions according to the use thereof in adult patients, children or newborns.

BRIEF DESCRIPTION OF THE DRAWINGS

Further characteristics and advantages will more fully emerge from the detailed description of some embodiments, provided by way of example, and thus not limiting to the aspects of the invention. The illustrated embodiments are described in the following, with reference to the accompanying drawings, which should be taken by way of non-limiting examples of the invention in which:

FIGS. 10A, 10B, 10C and 10D illustrate an extracorporeal blood circuit according to aspects of the invention.

DETAILED DESCRIPTION

With reference to the accompanying figures, 1 denotes in its entirety a collecting device of biological fluids for medical use. The device 1 is usable for various methods of extracorporeal circulation. As will be more fully described below, the exclusion, even temporary, of the device or reservoir 1, by activation of the bypass line associated thereto, produces an "active venous drainage" that enables the performance of various methods such as ECLS (extra corporeal life support), ECMO (extra corporeal membrane oxygenator), intra-operative ECMO. The device can further be used for treatments where it is necessary to store blood, blood derivative products and/or fluids and return or introduce them into the patient undergoing treatment.

Figure 1:
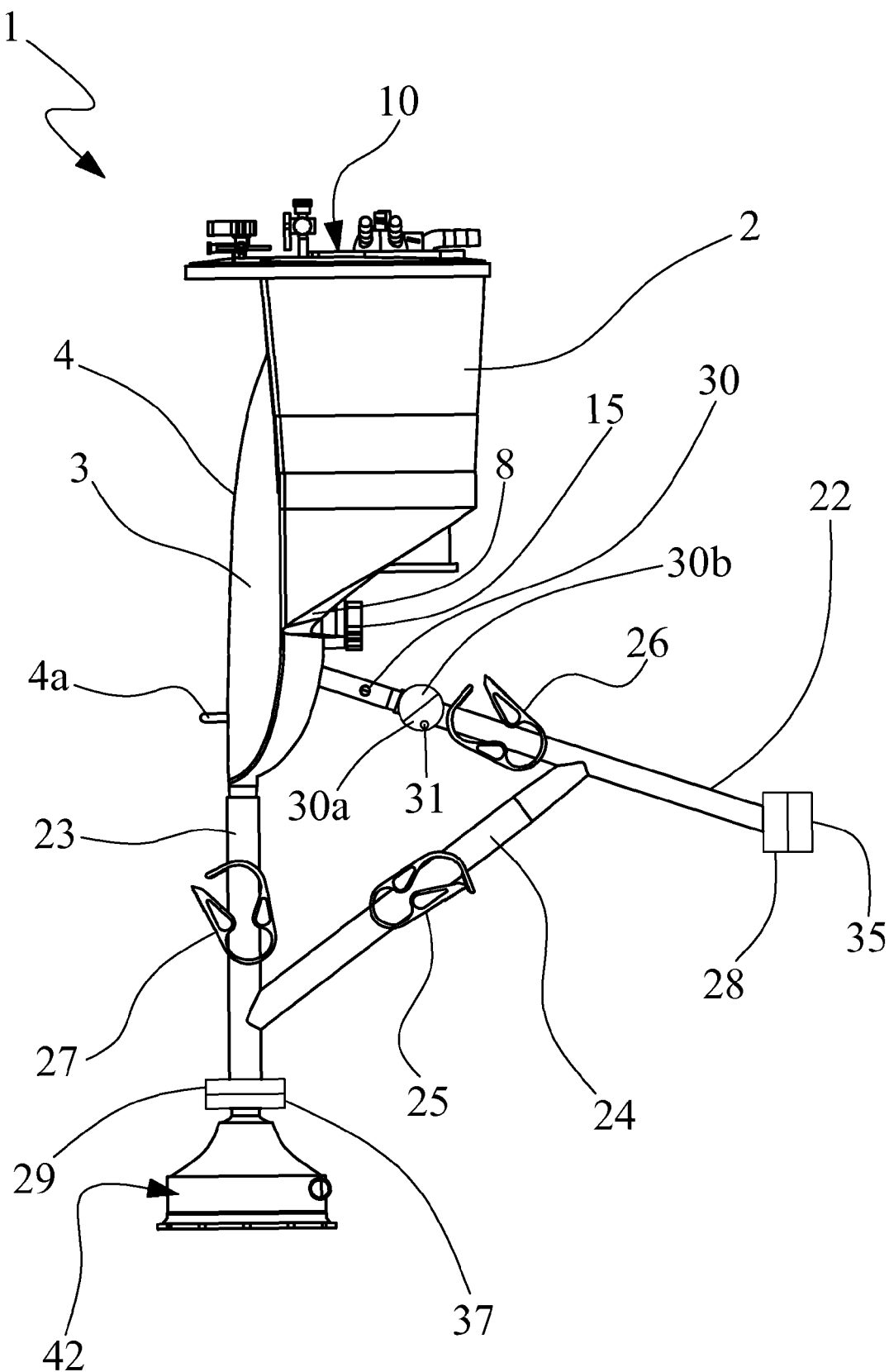
FIG. 1 is a collecting device of biological fluids according to aspects of the invention in lateral elevation.
Figure 4:
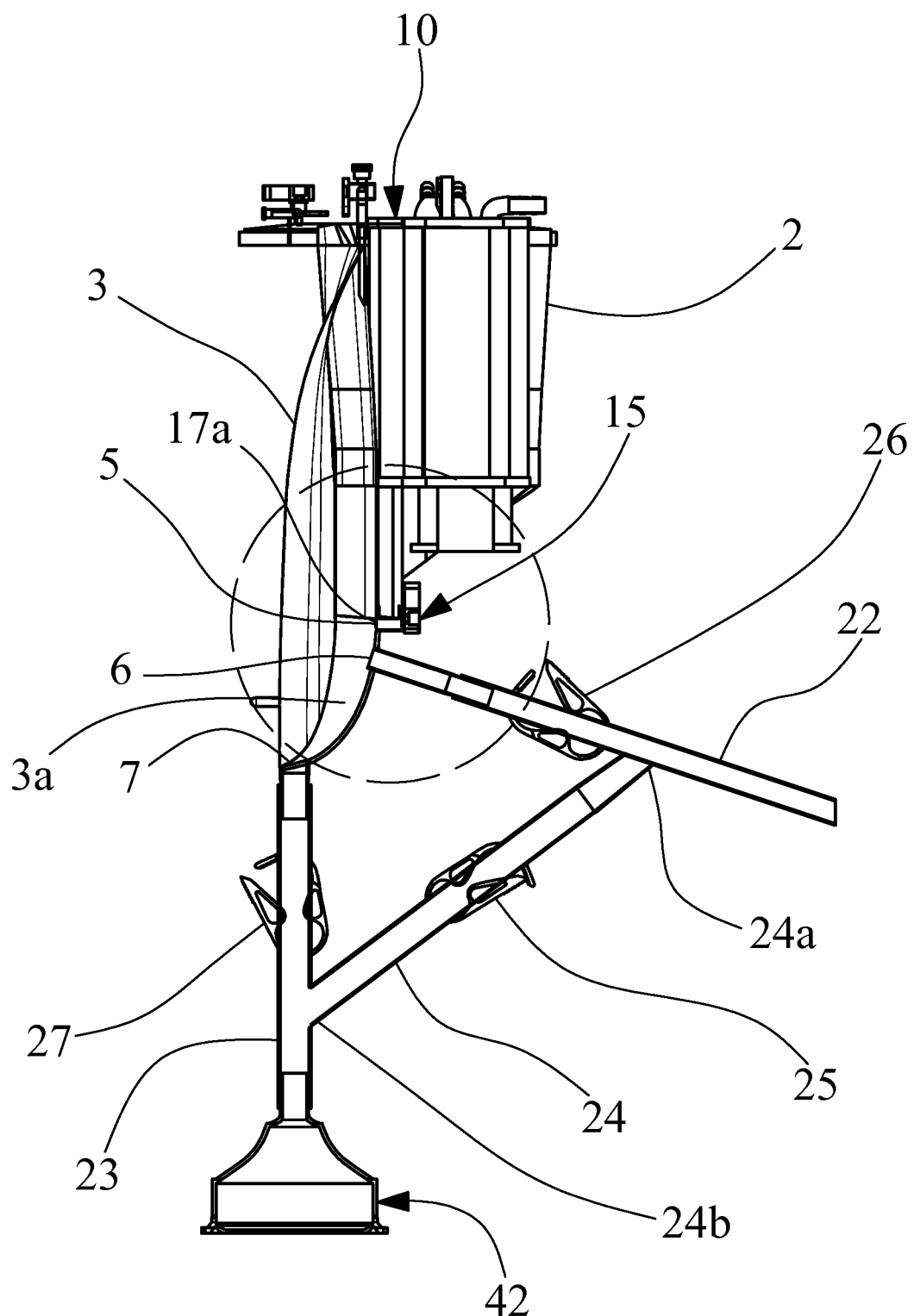
FIG. 4 illustrates a section of the collecting device of FIG. 1.

As shown in FIGS. 1 and 4, the collecting device 1 comprises a rigid container 2 flanked to an auxiliary container 3. The rigid container 2 comprises a bottom wall 8 which in the illustrated example is inclined from top to bottom in a nearing direction to the auxiliary container 3, and a lateral wall 9 emerging substantially vertically, or with a certain flaring, from the bottom wall 8. A closing portion 10 or end wall is then applied to the top of the lateral wall 9; under operating conditions the closing wall 10 develops substantially in a transversal direction to the lateral wall.

Figure 2:
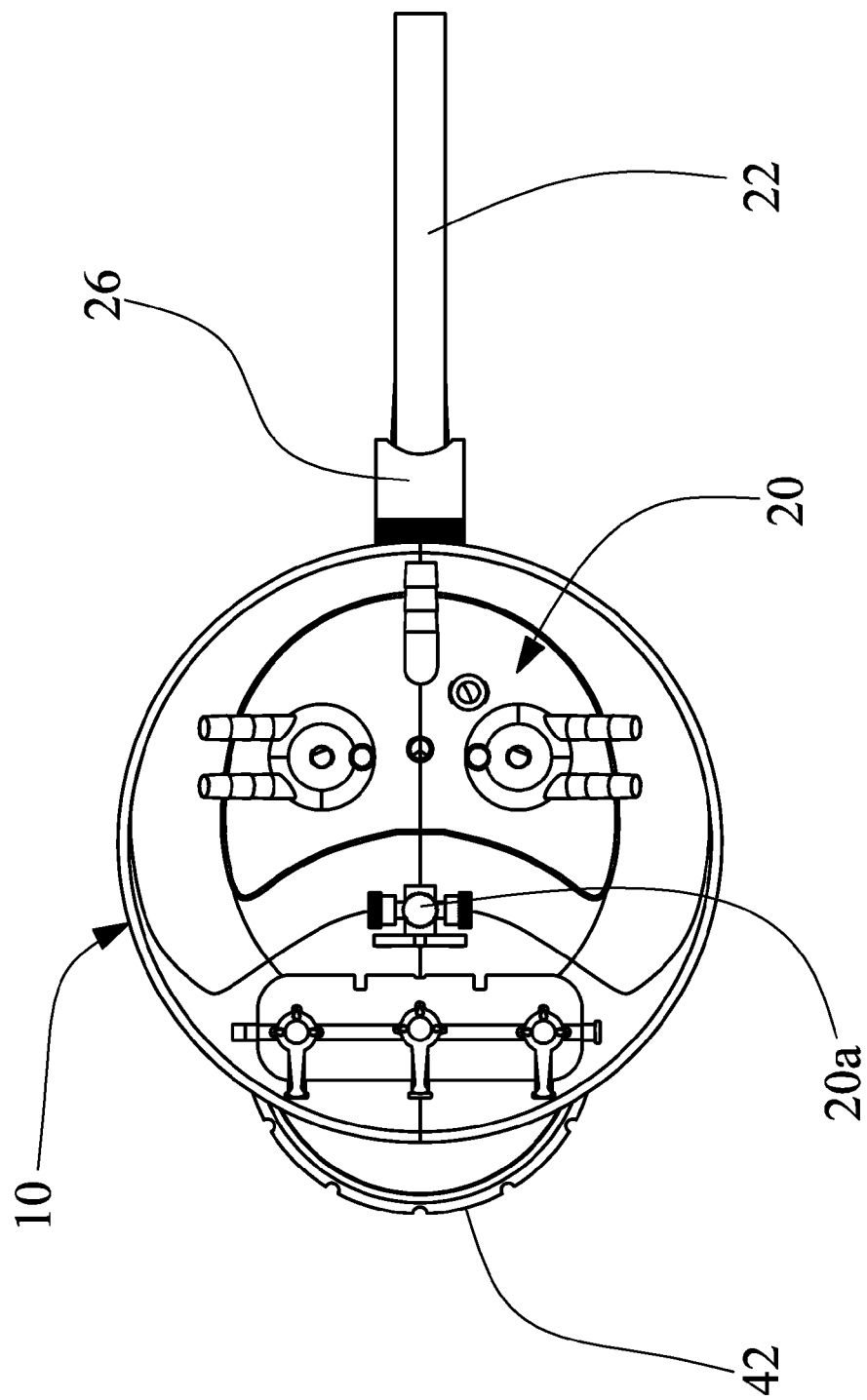
FIG. 2 is the collecting device of FIG. 1, in a plan view from above.
Figure 3:
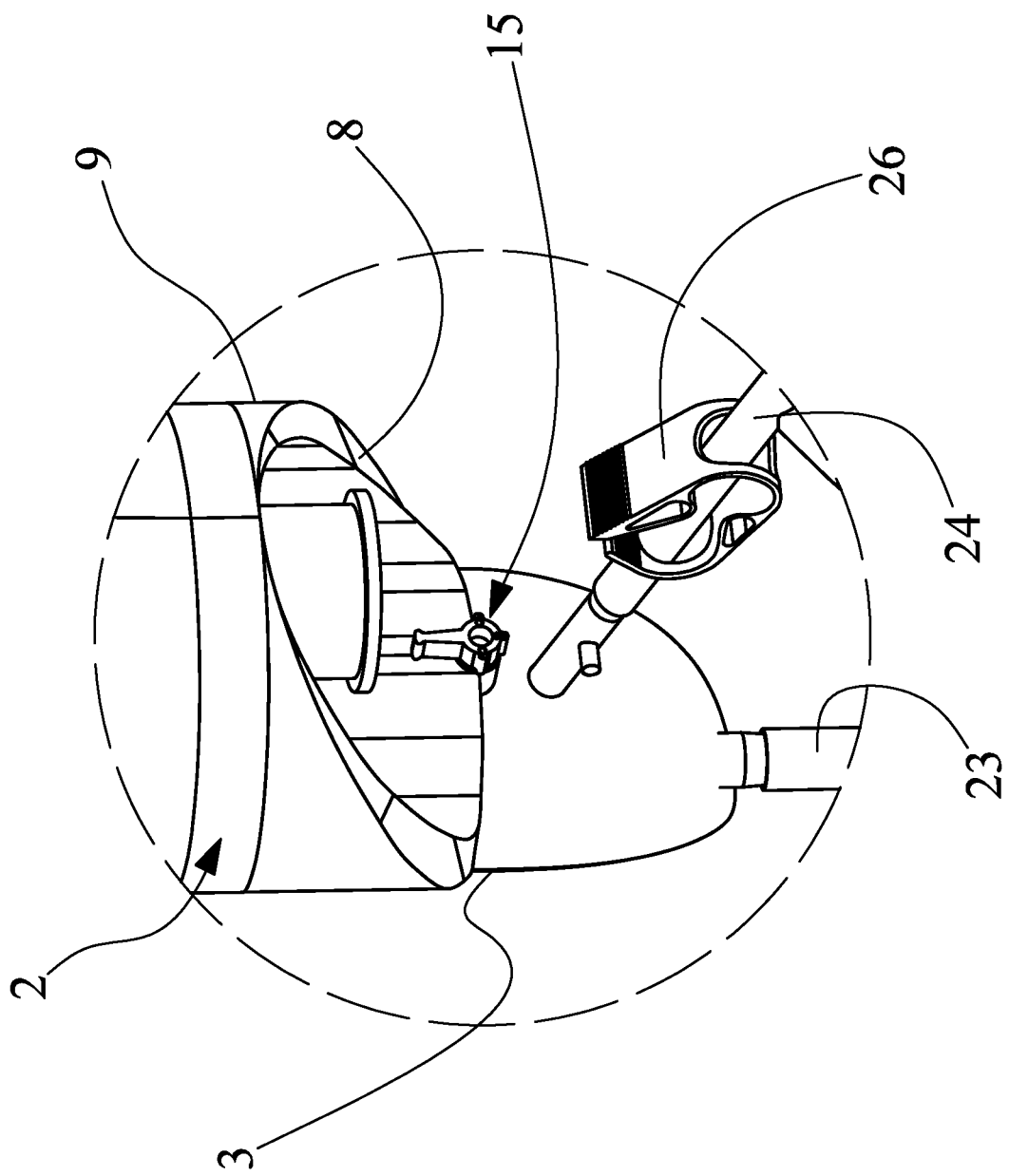
FIG. 3 shows, in a perspective view, a detail of the collecting device relating to a lower part thereof.

In more detail, the closing portion 10 is a cap connected to the top of the lateral wall 9 of the rigid container 2. As shown in FIG. 2, the closing portion 10 includes, but is not limited to, one or more access elements which are configured such as to set the rigid container 2 and/or the auxiliary container 3 in communication with the outside atmosphere.

Still more specifically still, the closing portion 10 comprises various connectors denoted in their entirety with 20, including: at least a connector, for example with a ⅜" diameter, for an auxiliary inlet filter line which enables entry of filtered blood into the rigid container 2; a plurality of connectors with a ¼" diameter (in the example of FIG. 2 at least four) for connection with inlet filter lines that can be used for connection to aspirating lines, not shown, predisposed to receive blood from the operating field (this blood requires filtering before possible re-entry thereof into the patient's cardiovascular system) or for connecting to arterial-venous circulation lines. The closing portion 10 may also comprise a three-way tap 20a suitable for setting the auxiliary container 3 in communication with environmental air.

The closing portion 10 can further be accompanied by a vertical inlet for the infusion of priming liquid, various Luer Locks provided with screw caps, a ramp for collections, a Luer connector connected, via a hose (not shown), to the bottom of the reservoir for collection of blood outside of the cardiotomy, by aspiration.

Detailing the structure of the rigid container, the bottom wall 8, the lateral wall 9 and the closing portion 10 define a first chamber 2a internal of the rigid container 2 having a predetermined volume. For example, the volume of the first chamber may vary in case of device size: for "adults" it can be in a range of between 250 and 3000 $cm^3$; while for pediatric and newborn size, the volume is reduced proportionately.

The auxiliary container 3 is arranged in an immediately adjacent position to the rigid container 2, which auxiliary container 3 in the example shown in FIG. 1 comprises at least a deformable portion 4, in the case of FIG. 1 defined by a flexible wall, which contributes to defining a second chamber 3a having a variable volume depending on the configuration of the deformable portion. The range of the volume 3a of the chamber is reduced in pediatric and newborn sizes.

From the constructional point of view, the auxiliary container 3 can be made from a bag entirely formed by flexible walls closed on themselves so as to define a second deformable chamber, or alternatively the auxiliary container 3 can comprise a flexible wall fixed to one or more rigid walls. In the example illustrated in FIGS. 1 and 4, the auxiliary container 3 is made as follows: the flexible wall is sealedly fixed at a peripheral edge thereof to one or more of the rigid walls of the rigid container 2. In the present example the flexible wall is fixed to a portion of the lateral wall 9 of the rigid container 2. This portion of the lateral wall 9 of the rigid container 2 thus becomes a dividing wall in common between the rigid container 2 and the auxiliary container and separates the first and the second chambers 2a, 3a. This dividing wall between the first and second chambers is concave, from the side facing the auxiliary container, and acts as a rigid support for the flexible wall that can have the same shape and the same dimensions as the dividing wall.

Figure 5:
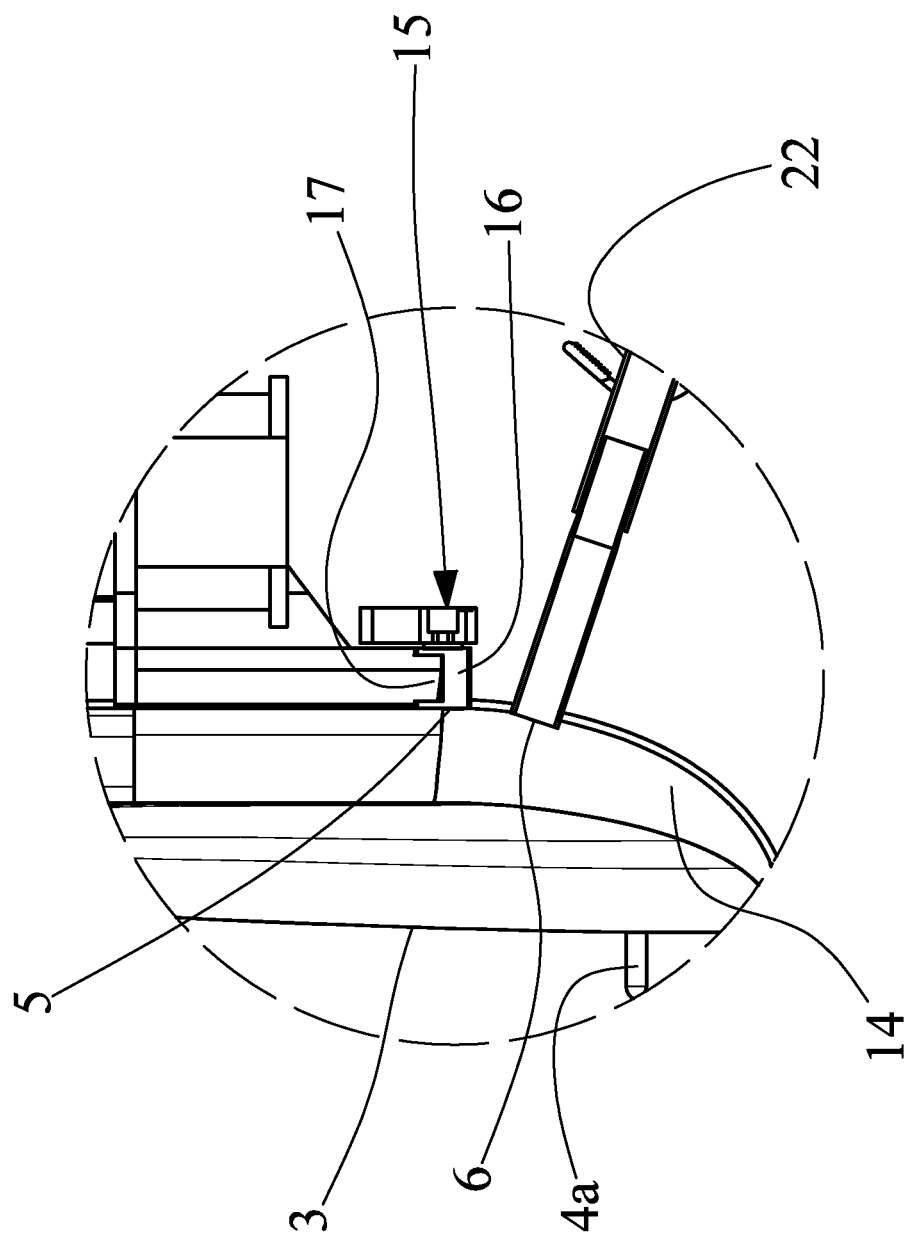
FIG. 5 is a detail of FIG. 4 relating to an open-shut tap of the passage which sets in fluid communication a first and second chamber of the device according to aspects of the invention.
Figure 6:
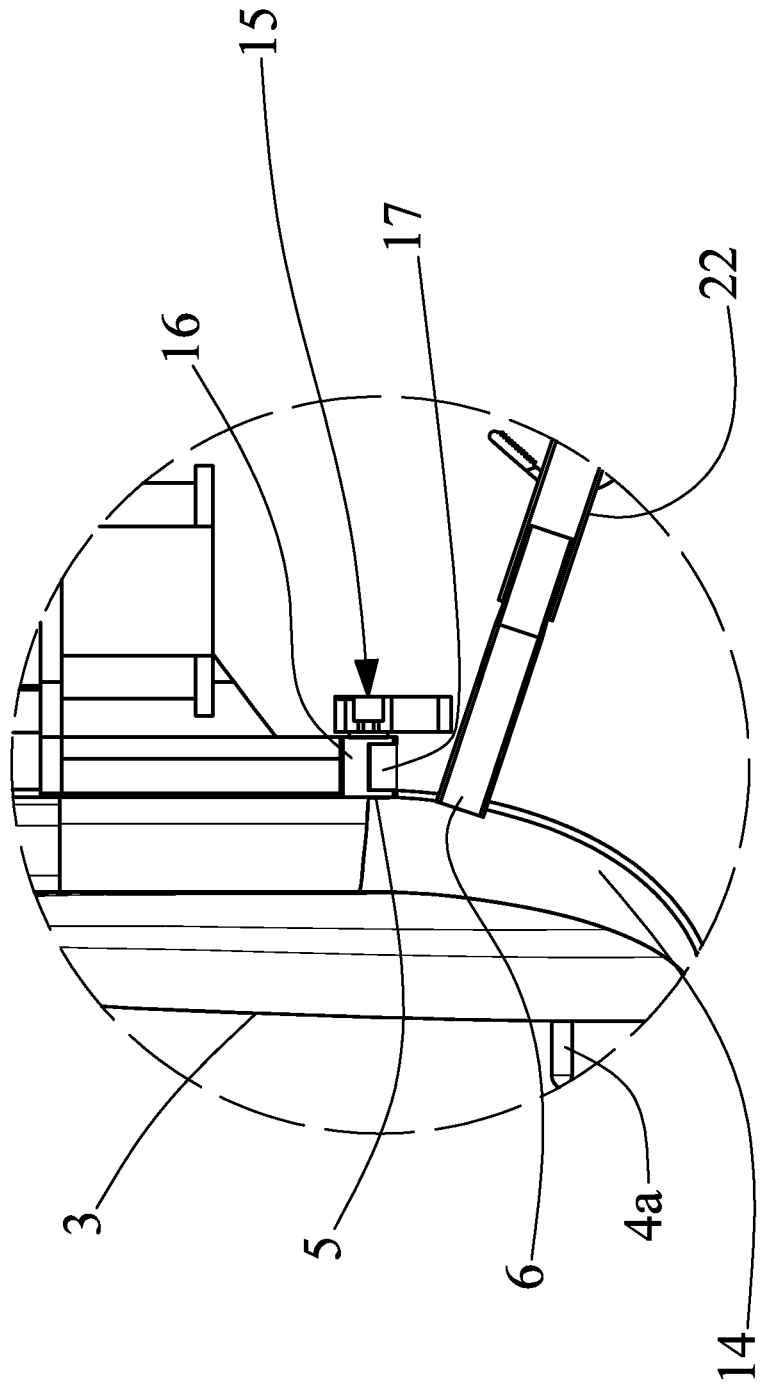
FIG. 6 also illustrates a detail of the tap of the preceding figure in a fluid intercepting condition.
Figure 7:
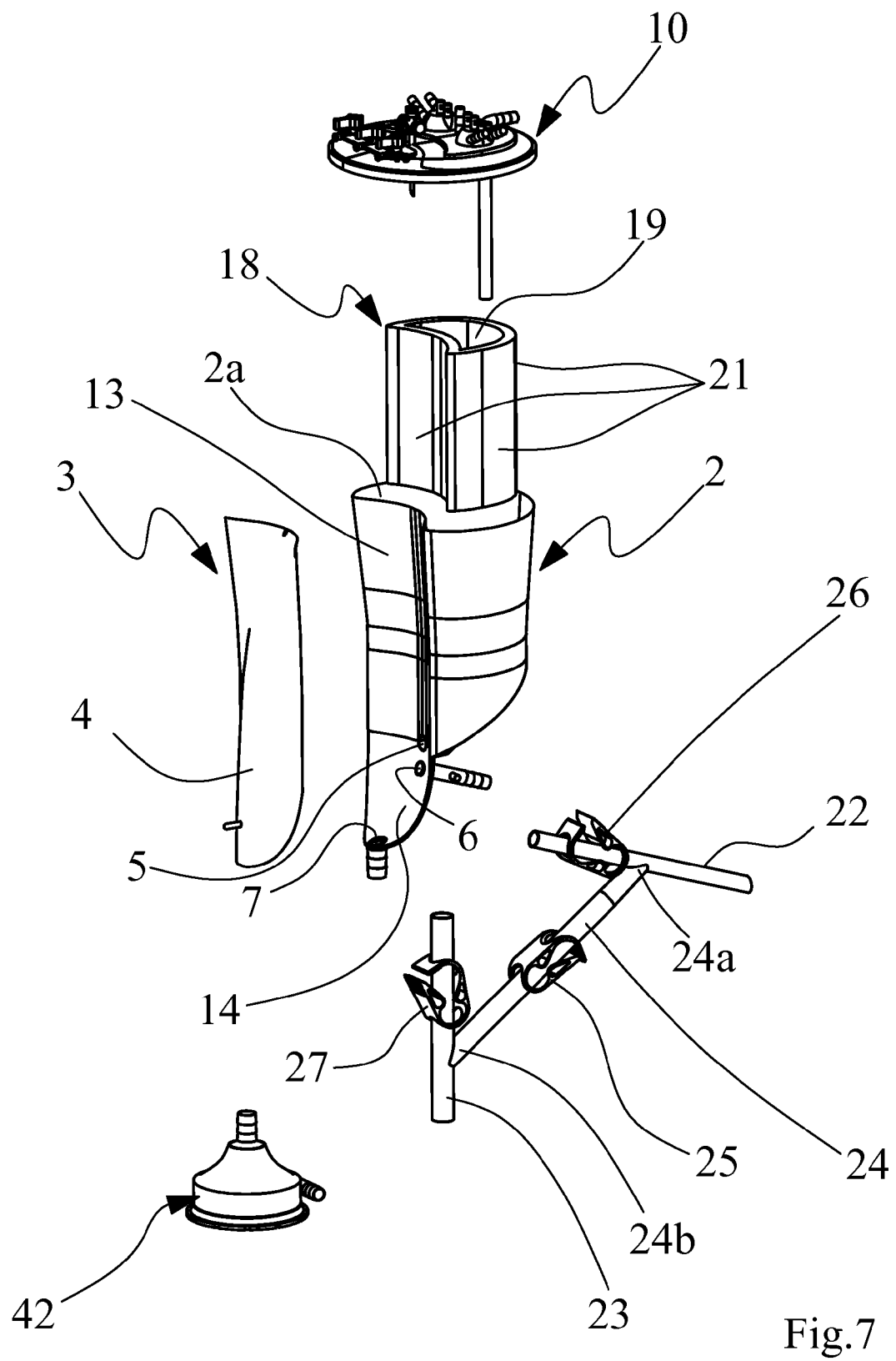
FIG. 7 is an exploded view of the biological fluid collector device of FIG. 1.

Alternatively, as already mentioned, it is possible that the auxiliary container 3 can be defined by a deformable bag fixed adjacent to the rigid container 2. In any case, the collecting device 1 comprises at least a passage 5 which places the first chamber 2a in fluid communication with the second chamber 3a. A fluid intercept member 15 is provided at the passage 5, for example equipped with a tap that can be activated from the outside or connected to an actuator member operated by a control unit, which can selectively open and close the fluid passage between the first and the second chamber 2a, 3a. As can be seen in detail in FIGS. 4, 5 and 6, the fluid intercept member 15 substantially comprises a wall element 16, which can for example comprise a tap actuating a selector having a cylindrical tubular shape and having a terminal opening 17a facing into in the second chamber 3a and a passage opening 17 extending on the lateral wall of the cylindrical surface of the selector.

Depending on the angular position of the tap activating selector, the passage opening 17 on the lateral wall can open up and face into the first chamber 2a, thus placing the first and the second chamber 2a, 3a in fluid communication (the condition shown in FIG. 5), or vice versa can face onto a bottom portion of the rigid container 2, which thus acts to close the opening. In other words, the angular rotation of the tap causes an angular rotation of the cylindrical selector which thus displaces between a position for fluid communication between the first and the second chamber 2a, 3a and a position of obstructing the said fluid communication.

With reference to FIGS. 4, 5, 6 and 7, the device 1 of the collection comprises at least an inlet port 6 for example connected to the second chamber 3a and an outlet port 7, also for example connected with the second chamber 3a. In particular, the device comprises a further rigid part 14 emerging in a downwards direction, for example, in continuation of the lateral wall 9 of the rigid container 2 and defining, with the portion of lateral wall 9 of the rigid container 2 one of the two halves which define the auxiliary container 3, the second semi-part being formed by the flexible wall that attaches to the rigid half by means of tight coupling of the perimeter edges of the flexible wall on the rigid portion, as already described.

As can be seen in the accompanying figures, the inlet port 6 and the outlet port 7 of the device 1 are made at the rigid part 14 extending in continuation of the lateral wall 9 of the rigid container 2 inferiorly of the first chamber 2a. More precisely, the outlet port 7 is localized in the area of the second vertically lower chamber 3a, while the inlet port 6 is located below the fluid communication passage 5 between the first and the second chamber 2a, 3a, but superiorly with respect to the outlet port 7.

As illustrated in FIG. 4, the rigid portion extending below the first chamber 2a has a curved conformation such as to facilitate the outflow of fluid from the inlet port 6 to the outlet port 7 or in any case, more generally, the outflow of fluid towards the outlet port 7. Further, the arched shape of the part 14, together with the concavity thereof facing the inside of the second chamber 3a, during emptying of the second chamber facilitate the support of the deformable portion 4 on the inner surface of the part 14. The deformable wall or membrane 4 adheres perfectly on the outlet hole, so that in a case of decrease in the level of liquid, the membrane 4 collapses onto the rigid support and, therefore, onto the outlet hole, preventing the accidental entry of air into the extracorporeal circuit.

In proximity of the outlet hole the exterior of the membrane 4 is provided with a silicone tab 4a which enables pulling out the membrane while preventing the collapsing thereof.

A discharge channel 23 is provided at the outlet port 7 and fixed thereto, while a supply channel 22 is fixed to the same inlet port 6, while at the inlet port 6 there is a supply channel 22 fixed to the inlet port 6. A bypass channel 24 is provided transversally of the supply channel 22 from the discharge channel 23, which bypass channel has a first end 24a connected with the supply channel 22 and a second end 24b opposite the first end 24a and connected to the discharge channel 23. A fluid intercept member can be provided in the portion of the discharge channel 23 comprised between the outlet port 7 and the second end 24b of the bypass channel 24, in the stretch of supply channel 22 comprised between the inlet opening 6 and the first end 24a of the bypass channel 24, as well at the bypass channel 24. In particular, the accompanying figures non-limitingly illustrate a condition in which intercept members 25, 26, 27 are provided in the bypass channel, the supply channel and the discharge channel.

In the example illustrated in the accompanying figures, the intercept valves 25, 26, 27 valves comprise a clip that can be activated manually between a condition of clamping of the tube, in which passage of fluid in the respective portion is inhibited, and a release condition in which the passage of fluid through the tube can be converted. By selectively activating the three clamps present on the sections of pipe it is possible to obtain different operating conditions of the collecting device, as will be more fully clarified in the following.

Alternatively to the described clamping devices, fluid intercept members of a different nature can be used, for example manually-controlled valves, or alternatively valves controlled by actuators managed by a control unit.

In accordance with an aspect of the invention, the channels 22, 23, and 24 can be preformed in a single piece or pre-assembled (for example glued or welded) to one another and to one or the other of the containers 2 and 3.

As can be seen in FIG. 1, the device 1 can further comprise at least an ampoule 30 operatively connected upstream of the inlet port 6 and internally comprising at least a hydrophilic membrane which can enable passage of liquid from an upstream section of the bulb 30 towards a downstream section thereof by reducing the passage of gas (thus acting as a de-foaming membrane). As shown in the accompanying figures, the bulb 30 is non-limitingly located at the supply channel 22 such as to intercept the fluid directed to the containers and passing through the inlet port 6. With regard to the membrane arranged in the ampoule 30, said membrane separates the upstream section from the downstream section respectively into an upstream semi-chamber 30a and in a downstream semi-chamber 30b. In particular, the upstream semi-chamber 30a includes, but is not limited to, a passage 31 that can be used for the evacuation of gas.

Figure 1A:
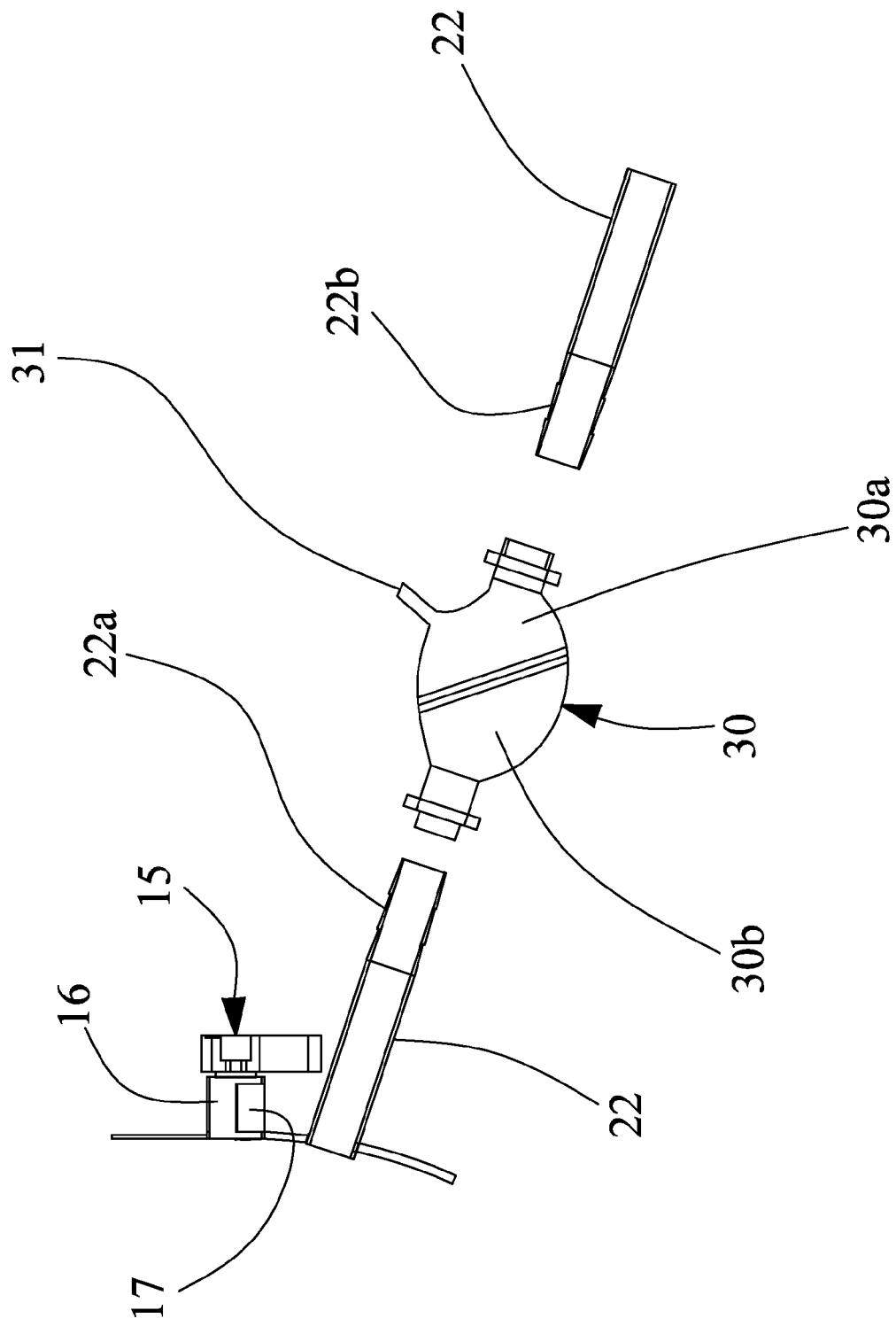
FIG. 1A is a detail of the device of FIG. 1.

FIG. 1A illustrates a detail of the ampoule inserted in the supply channel 22 between two Luer connections 22a and 22b (of large dimensions, for example ½ inch). Note that for example the ampoule 30 can operate in a portion interposed between the inlet into the chamber 3a and the junction between the channel 22 and the bypass channel 24.

Both the supply channel 22 and the discharge channel 23, at respective opposite ends to the inlet and outlet ports 6, 7, comprise removable connector elements 28, 29, for example large luer-type connectors (½" for the adult reservoir, ⅜" for the pediatric device and ¼" for the newborn device) for detachable coupling of the collecting device 1 in an extracorporeal circuit 100, as shown in FIG. 1.

The Luer connectors, being connected to the device by the interposing of a clampable tube (welded) facilitate replacement of the device in case of malfunction thereof.

The collecting device 1 also comprises a filter element 18 located at the upper zone of the first chamber 2a and having an access side 19 positioned in fluid communication with an inlet of fluid to be filtered and an outlet side 21 of the filtered fluid directed towards the lower zone of the first chamber 2a, so as to deliver the filtered fluid.

In greater detail, the filter element 18 is configured to receive the fluid introduced in the first chamber 2a through the access side via the auxiliary inlet opening 20, and provide filtered fluid from the outlet side 21.

Figure 8:
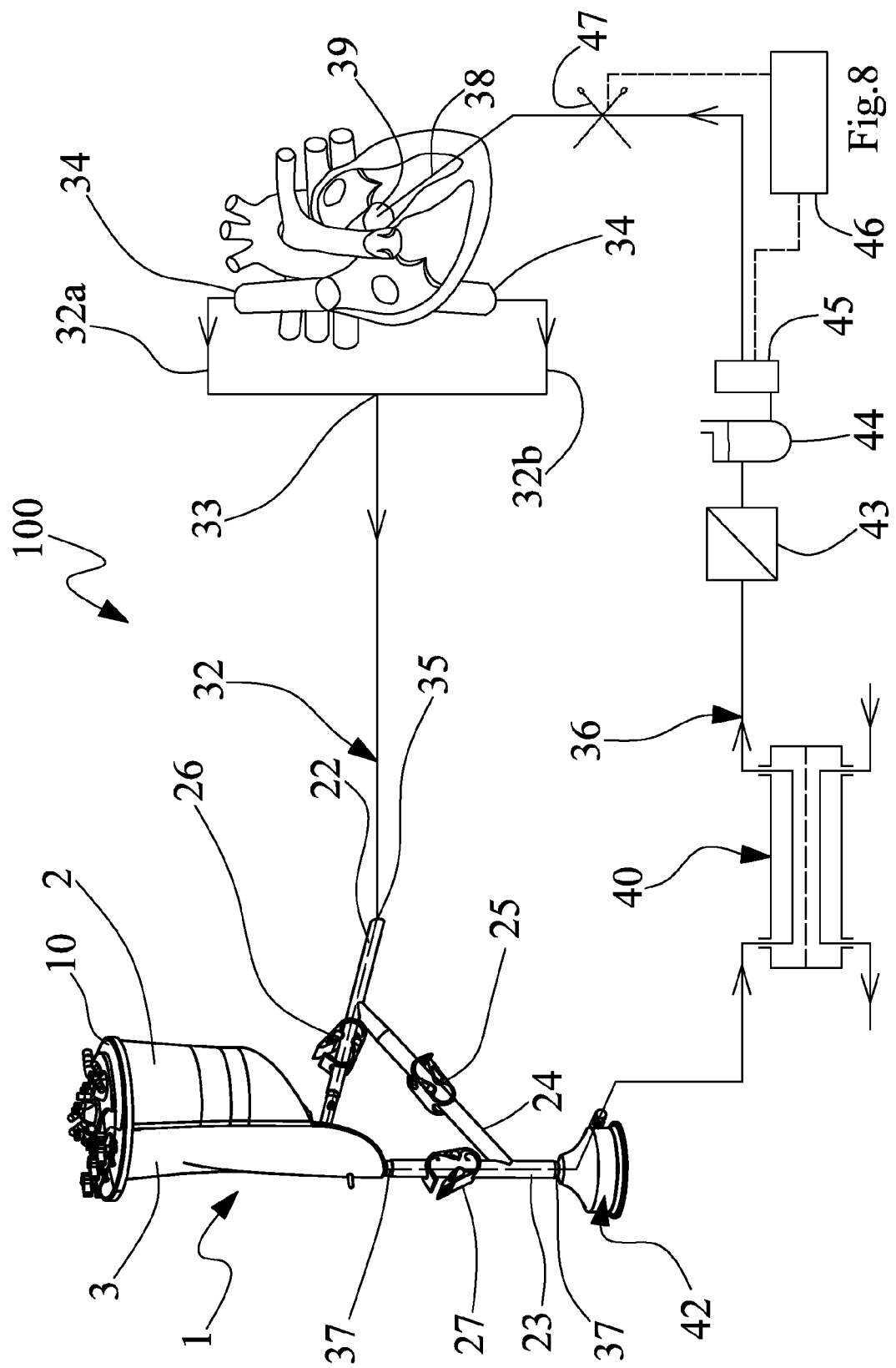
FIG. 8 illustrates an extracorporeal circuit in which the device of FIG. 1 is included in a first operating condition in which the bypass line of the device is closed.
Figure 9:
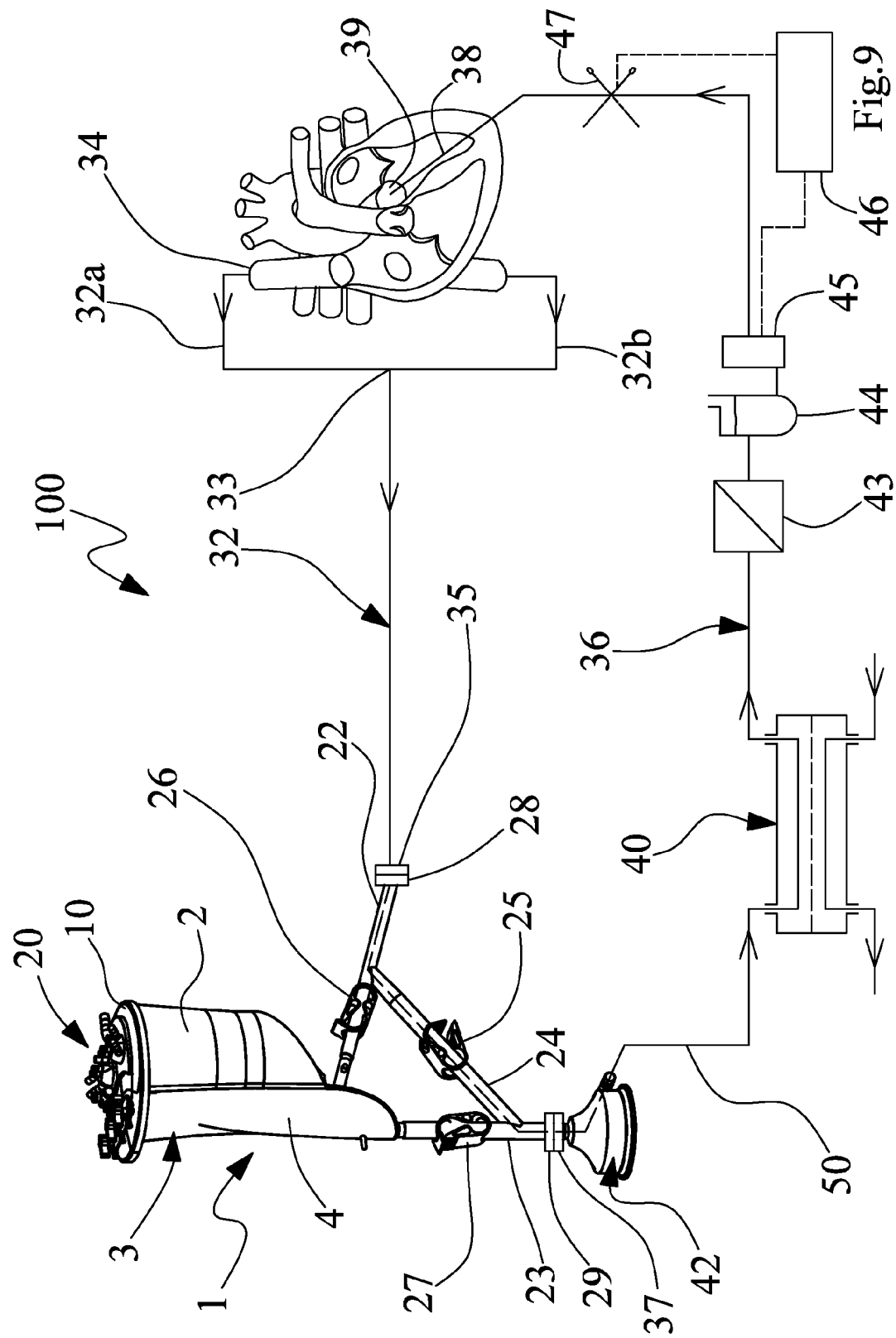
FIG. 9 is an extracorporeal blood circuit in which the device of FIG. 1 is included, in a second operating condition in which the bypass line of the device is open, while the fluid supply and return channels are closed, respectively entering and exiting the collecting device.
Figure 10B:
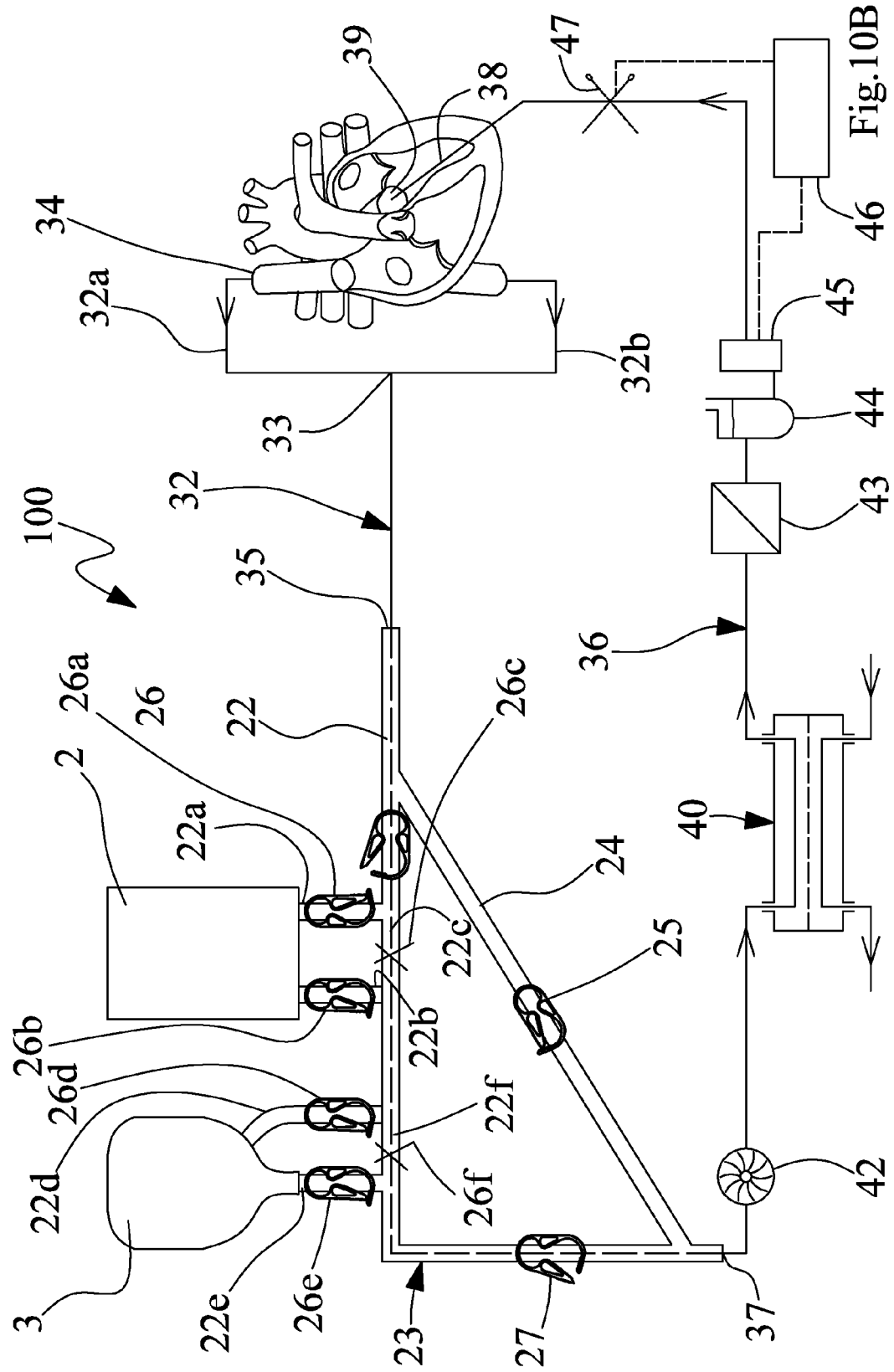
Figure 10D:
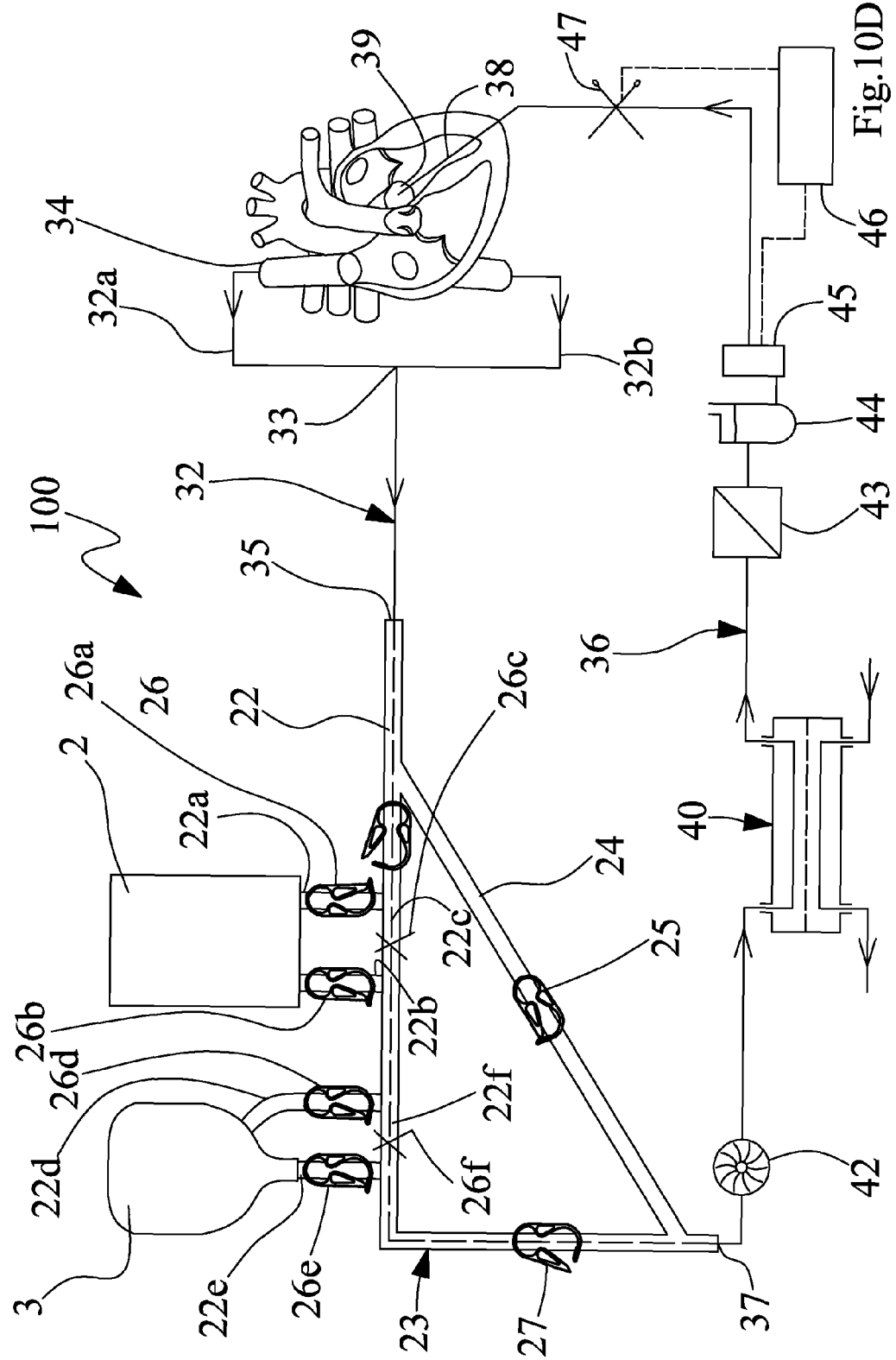

As can be seen in FIGS. 8 and 9, the collecting device 1 can be inserted in the extracorporeal blood circuit 100 which has a removal line 32 and a blood return line 36 to the patient; in practice the collecting device 1 is inserted so as to connect the connector 28 of the supply channel 22 to a second end 35 of the collecting line 32, also connecting the connector 29 associated to the discharge channel 23 at a first end 37 of the return line 36. In this way, the collecting line 32 can receive the venous blood and send it towards one or both chambers of the collecting device 1 while the return line 36 can return the blood exiting from the collecting device 1 towards the patient. In the example illustrated in FIGS. 8 and 9, the collecting line has two branches 32a, 32b for collecting blood from the patient, respectively connected to accesses 34 (for example connected to the upper and lower vena cava).

Note that a treatment unit is provided for example on the return line 36, such as an oxygenation device 40 operating such as to provide an adequate oxygenation of the blood to be returned to the patient. The oxygenating device may include various types of membrane: microporous, made of polymethylpentene, etc.

Further treatment units can be provide, such as a heat exchanger (e.g. integrated in the oxygenator 40), a filter 43, an air bubble separator 44, an air bubble detecting organ 45 and other units besides, depending on the type of treatment to be imparted on the blood.

In greater detail, the above-described units are arranged on the blood return line 36. In particular, as visible from the accompanying figures, the oxygenation device 40 is arranged downstream of the collecting device 1. Downstream of the oxygenation device the following are non-limitingly arranged: in order, the filter 43, the air bubble separator 44 and the air bubble detecting organ 45.

The collecting device 1 can further comprise a control unit 46 connected with at least one of the units mentioned above and can be configured to control and manage at least one of the units.

The control unit 46 is also configured to receive a control signal from the air-bubble detector 45 and possibly command at least one intercept valve 47 arranged downstream of the air-bubble detector 45 such as to prevent any entry of air bubbles into the patient.

In order to move the blood along the return line 36 and in fact along the entire extracorporeal circuit, a pump 42 can be provided, located downstream of the collecting device 1 and operating for example on a part of the return line 36 of the blood to the patient between the oxygenator 40 and the outlet port 7 of the collecting device 1. From the constructional point of view the pump 42 can be a peristaltic-type pump (with rollers), a centrifugal-type pump, or another type, as long as it capable of moving a fluid without damaging a delicate fluid, namely blood.

A variant of the invention is shown in FIGS. 10A-10D. In particular, the device 1 comprises in this case at least one rigid container 2 and at least one auxiliary container 3, which may include, but are not limited to, the same characteristics as the containers described above. At least one of the containers comprises at least an inlet port 6 and an outlet port 7; in particular, as shown in FIGS. 10A to 10D, each container comprises a respective inlet port 6 and a respective outlet port 7. The device 1 comprises a supply channel 22 in fluid communication with the collecting line 32, suitable for collecting blood from the patient. The supply channel 22 comprises at least a first channel 22a and at least a second channel 22b which set the supply channel 22 in fluid communication with the rigid container 2.

In greater detail, the first channel 22a emerges transversally to the supply channel and connects to the inlet port 6 of the rigid container 2. The second channel 22b also emerges from the supply channel 22 and connects to the outlet port 7 of the rigid container 2. As shown in the accompanying figures, the supply channel can also optionally comprise a tract 22c which places the first and the second channel 22a, 22b in fluid communication. A respective intercept member 26a, 26b can operate on the first and second channel 22a, 22b and be configured such as to be arranged selectively in an enable or inhibit condition of the fluid passage through the channel on which the intercept member is applied.

The supply channel 22 may further comprise a third and a fourth channel 22d, 22e which place the supply channel 22 in fluid communication with the auxiliary container 3. In more detail, the third channel 22d emerges transversally of the supply channel 22 and connects to the inlet port 6 of the auxiliary container 3. The fourth channel 22e also emerges from the supply channel 22 and connects to the outlet port 7 of the auxiliary container 2. As shown in the accompanying figures, the supply channel may optionally further comprise a portion 22f which places the third and the fourth channel 22d, 22e in fluid communication. A respective intercepting member 26d, 26e operates on the third and fourth channel 22d, 22e, which member 26d, 26e is configured such as to be selectively arranged in an enabling or inhibiting condition of fluid passage through the channel on which the intercept member is applied. Downstream of the channels 22a, 22b, 22d, 22e, and in continuation of the supply channel 22 a discharge channel 23 is provided which carries the fluid to the return line 36 where the same components can operate (pumps, heat exchanger, oxygenator, bubble trap or arterial filter) as those described with reference to the solution of FIGS. 1-8.

A by-pass channel 24 enables connection of the supply channel 22 directly with the discharge channel 23, bypassing the containers 2 and 3, as shown in FIGS. 10A-10D. In particular, the by-pass channel 24 has a first end 24a connected with the supply channel 22 upstream of the first channel 22a and a second end 24b connected with the discharge channel 23 downstream of the fourth channel 22e. In a further variant, the containers 2 and 3 may be connected by a passage 5 on which an interception element 15 can operate: in this case the channels 22b, 22c, 22f and 22d might not be necessary since, as the two containers 2 and 3 connected by the passage 5 and having at least one inlet channel and one outlet channel, the device would still be able to exploit the capacity of both containers 2 and 3.

Following the above description, made in terms substantially relating to the structural operation of the device 1 and of the extracorporeal circuit 100 illustrated in FIGS. 1 to 8, the functioning of the device is as follows.

After connecting the device 1 to the rest of the extracorporeal circuit it is possible to proceed with the washing or "priming" operations using, for example, the container 2 in which "priming" fluid, for example saline, can be made to flow. Once the "priming" has been completed, the circuit 100 can be connected to the patient; then, by acting appropriately on the members 25, 26 and 27, one of the following modes can be selected:

bypass mode, in which the device 1 is excluded from the extracorporeal circuit because the bodies 26 and 27 are closed while the organ 25 is open. In this mode, the blood can be, for example, oxygenated, but without use of any fluid present in one or other of the two containers 2, 3 which are therefore excluded from the circuit 100;

a mode with the device 1 active and the intercept member 15 closed: in this case the bodies 26 and 27 are open while the organ 25 is closed. In this operating mode, the extracorporeal circuit exploits only the volume of the deformable container 3, in effect operating as a closed circuit substantially without—or with only minimum—contact with air. The fluid collected from the patient proceeds in the venous branch, accedes to the container 3 through the inlet port 6, exits from the outlet port 7, reaches the pump 42, passes through the oxygenator 40 and any other units and then returns to the patient through the second end 38 of the return line. In a case in which the container 3 where the blood is stored empties, the deformable portion 4 of the container 3 rests on the internal surface of the part 14, closing the outlet port 7; in this regard, note that a tab or other gripping element 4a can be provided, emerging from the deformable portion 4 which can be used to facilitate the separation of the deformable portion from the part 14;

a mode with the device 1 active and the tap open: in this case too the organs 26 and 27 are open while the organ 25 is closed. In this operating mode, the extracorporeal circuit exploits both the volume of the deformable container 3 and the volume of the rigid container 2, effectively operating as an open system with a high capacity of blood or other fluid accumulation. Note that in this case the rigid container can receive the blood coming from the operating field and as such comprising clots, bone fragments and tissue, fat and other substances that can be appropriately filtered by the filter present in the rigid container 2. In this case too the fluid collected from the patient proceeds in the venous branch, accedes to the deformable container 3 and also to the container 2, the two containers being connected by the passage 5. The blood then exits from the port 7, reaches the pump 42, passes through the oxygenator 40 and any other units and then returns to the patient through the second end 38 of the return line; as mentioned it is possible for the container 2 also to receive blood or other fluids through connectors for aspiration, infusion or arterial-venous circulation lines. In this operating mode, however, the level of fluid in the containers 2 and 3 is practically the same as the two containers are connected. Obviously, in case of need, the operator can disconnect the communication between the two containers simply by acting on the intercept member 15.

Finally it should be noted that the device and the circuit described may be used sequentially in the ways described. For example it is possible, after priming, to start in the operating mode 1 with the device active and the intercept member 15 closed. In this operating mode it is however possible to store any blood coming from the operating field in the container 2. In a following step it is for example possible to switch the operating mode with the device 1 active and intercept member 15 open, thereby draining the blood present in the container 2 to the container 3 and then towards the return line. More generally, by acting on the intercept member 15 and the bodies 25, 26, 27, any combination of the temporally sequential operating modes described above can be performed.

The operation of the device 1 and of the extracorporeal circuit 100 illustrated in FIGS. 10A to 10D is as follows.

After connecting the device 1 to the rest of the extracorporeal circuit 100 the washing operations or "priming" operations can be proceeded to, using, for example, the container 2 and/or the deformable container 3 in which the "priming" fluid flow can be made to flow. Once the "priming" has been completed, the circuit 100 can be connected to the patient and by acting on the intercept members arranged on the supply, discharge and bypass channels, one of the following modes can be selected:

bypass mode, in which the device 1 is excluded from the extracorporeal circuit because the bodies arranged on the supply channel and/or on the discharge channel are closed while the intercept member arranged on the bypass channel is open. In this mode, the blood can be oxygenated, for example, but without use of any fluid present in one or other of the two containers 2, 3 which are therefore excluded from the circuit 100.

Mode with device 1 and active use of the auxiliary container 3: in this case at least a part of the intercept members positioned on the supply channel are open while the intercept member positioned on the bypass channel is closed; in more detail the intercept members 26a, 26b are closed while the intercept members 26c, 26d, 26e and 26f are open; in this operating mode, the extracorporeal circuit exploits only the volume of the auxiliary container 3, effectively operating as a closed circuit substantially without or with minimal contact with air; the fluid collected from the patient proceeds in the venous branch, accedes to the container 3 through the inlet port 6 in communication with the channel 22d, exits from the port 7 in fluid communication with the channel 22e, reaches the pump 42, passes through the oxygenator 40 and any other units and then returns to the patient through the second end 38 of the return line;

mode with device 1 active and use of the rigid container 2: in this case at least a part of the intercept members arranged on the supply channel are open while the intercept member positioned on the bypass channel is closed; in more detail the intercept members 26d, 26e are closed while the intercept members 26a, 26b, 26f (and optionally 22c) are open. In this operating mode, the extracorporeal circuit exploits only the volume of the container 2, operating as an open circuit; the fluid taken from the patient proceeds in the venous branch, accedes to the container 2 through the inlet port 6 in communication with the channel 22a, exits from the port 7 in fluid communication with the channel 22b, reaches the pump 42, passes through the oxygenator 40 and any other unit and then returns to the patient through the second end 38 of the return line;

mode with device 1 active and use of both the rigid container 2 and the auxiliary container 3: in this case too at least one of the intercept members positioned on the supply channel is open while the intercept member arranged on the bypass channel is closed. In more detail, in order to exploit the volume of the two containers the intercept members 26a, 26b, 26d and 26e can be kept open while the intercept members 26c, and 26f can be closed; alternatively, if the device is provided with the passage 5, the channels 22b, 22c, 22d and 22f can be closed and the intercept members 26a and 26e kept open as well as the intercept member 15 arranged on the passage connecting the two containers; in this operating mode, the extracorporeal circuit exploits the volume of the deformable container 3 and the volume of the rigid container 2, operating effectively as an open system with high blood or other fluid storage capacity—note that in this case the rigid container can receive, from the connectors for the aspirating lines, blood from the operating field and as such comprising clots, bone fragments, and other elements that can be adequately filtered by the filter present in the rigid container 2; in this case too the fluid collected from the patient proceeds in the venous branch, accedes to the container 3 and also, possibly, to the container 2, the two containers being connected. The blood then exits from the port 7 of the auxiliary container 3, reaches the pump 42, passes through the oxygenator 40 and any other units and then returns to the patient through the second end 38 of the return line; as mentioned the container 2 can also receive blood or other fluid through the aspiration or infusion lines. In this operating mode, however, the level of fluid in the containers 2 and 3 is practically the same as the two containers are connected.

Finally it should be noted that the device 1 and the circuit 100 described may be used sequentially in the ways described. More generally, by acting on the intercept members any combination of the temporally sequential operating modes described above can be carried out.

From a constructional point of view, finally, the device 1 can be made of plastic material for medical use. In particular, the rigid container 2 is made of rigid plastic material while the deformable wall can be realized by a plastic film glued or welded to the wall provided on the rigid container 2. The various supply, unloading and by-pass channels can also be joined in a single piece to the container 3, by gluing or welding. Fixed connectors such as Luer connectors can be heat-joined to the supply and discharge channels, for easy engagement and disengagement of the device 1. The ampoule 30, when present, is also integrally joined to the device 1, for example welded or glued on the supply channel. The oxygenator can also be integrally joined to the device 1, upstream of the Luer connector associated with the discharge channel.

It will be apparent to those skilled in the art that various modifications and variations can be made to the device for medical use for collecting and transit of blood, blood derivatives and/or filler fluids, and extracorporeal circuit comprising the device of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. A collecting device for biological fluids for medical use, comprising:
   a rigid container exhibiting a box conformation having a bottom wall, a lateral wall emerging from the bottom wall, and a closing portion located at a top of the lateral wall, the bottom wall, the lateral wall, and the closing portion internally defining at least a first chamber having a fixed volume;
   an auxiliary container having at least a deformable portion which is constrained to at least a corresponding portion of the lateral wall of the rigid container, said auxiliary container internally defining a second chamber having a variable volume according to a position of the deformable portion;
   at least a passage able to set the first chamber and the second chamber in fluid communication;
   at least one inlet port connected with at least one of the rigid container and the auxiliary container; and
   at least one exit port connected with at least one of the rigid container and the auxiliary container, wherein
   the deformable portion of the auxiliary container comprises at least one deformable wall peripherally constrained to the lateral wall of the rigid container,
   the rigid container and the auxiliary container are mutually flanked, and
   a portion of the lateral wall of the rigid container separates the first chamber and the second chamber and constitutes a portion of wall in common between the rigid container and the auxiliary container.

2. The device of claim 1, wherein a protruding part emerges from a portion of lateral wall of the rigid container, with reference to an operating configuration in which the lateral wall extends from below in an upwards direction, the protruding part developing inferiorly with respect to the first chamber and in prolongation with respect to the lateral wall, and
   wherein the auxiliary container comprises:
   a rigid wall formed by a portion of the lateral wall of the rigid container and by the protruding part, and
   a flexible wall peripherally and sealedly fixed to the rigid wall of the auxiliary container.

3. The device of claim 2, wherein the protruding part exhibits an arched conformation having a concavity facing towards an inside of the second chamber.

4. The device of claim 1, wherein the passage, which sets the first chamber and the second chamber in fluid communication, is located at a bottom of the first chamber.

5. The device of claim 1, further comprising at least one fluid intercept element manually drivable from outside the device and operating at the passage setting the first chamber and the second chamber in fluid communication, the fluid intercept element being displaceable between a first operating position, in which a fluid passage is enabled between the first chamber and the second chamber, and a second operating condition, in which the fluid passage between the first chamber and the second chamber is prevented.

6. The device of claim 5, wherein
   the fluid intercept element comprises a wall element which is substantially cylindrical and rotatably engaged internally of the passage, and which has at an axial end thereof a fluid passage opening set in communication with the second chamber and further having a second fluid passage opening made at a lateral wall of the cylindrical surface, and
   following an angular rotation of the fluid intercept element, the opening located on the cylindrical wall is displaceable between a first position in which the second opening opens towards the first chamber and sets the first chamber in fluid communication with the second chamber, and a second angularly offset position with respect to the first position in which the second opening is closed by a corresponding part of the passage, thereby preventing fluid communication between the first chamber and the second chamber.

7. The device of claim 1, wherein
   the inlet port is directly connected to the second chamber so as to enable inlet directly to the second chamber,
   the outlet port is directly connected to the second chamber so as to enable outlet directly from the second chamber, and
   the inlet port and the outlet port are located, with reference to an operating condition of the collecting device, at a lower height with respect to the passage which sets the first chamber and the second chamber in fluid communication.

8. The device of claim 2 wherein the inlet port is located and connected to the protruding part and the outlet port is connected at a vertically lowest zone of said protruding part.

9. The device of claim 1, further comprising:
a supply channel fixed to the inlet port;
a discharge channel fixed to the outlet port;
a bypass channel having a first end connected to the supply channel and a second end connected to the discharge channel for bypassing the fluid collecting device;
a first intercept organ on the bypass channel;
a second intercept organ on the supply channel in a zone comprised between the inlet port and an end of the bypass channel;
a third intercept organ on the discharge channel in a zone comprised between the outlet port and another end of the bypass channel;
a first connector located on a terminal part of the supply channel opposite the inlet port; and
a second connector located on the discharge channel opposite the outlet port, the first connector and the second connector being configured to enable disengagement of the collecting device relative to a respective line of an extracorporeal circuit.

10. The device of claim 1, further comprising at least a housing connected upstream of the inlet port and internally comprising at least a hydrophilic membrane configured to (i) enable passage of fluid from a first section upstream of the housing towards a second section downstream thereof, (ii) reduce passage of air, the membrane being arranged internally of the housing, and (iii) separate the housing into an upstream half-chamber and a downstream half-chamber, a passage for gas evacuation being provided at the upstream half-chamber.

11. The device of claim 1, wherein the bottom wall of the first chamber is inclined downwards as it proceeds towards the second chamber, such that outflow of liquid is facilitated through the passage from the first to the second chamber.

12. A collecting device for biological fluids for medical use, comprising:
a rigid container exhibiting a box conformation internally defining at least a first chamber having a fixed volume;
an auxiliary container having at least a deformable portion, said auxiliary container internally defining a second chamber having a variable volume according to a position of the deformable portion;
at least a passage connecting the first chamber and the second chamber;
at least one inlet port directly connected to the second chamber so as to enable fluid to inlet directly into the second chamber; and
at least one outlet port directly connected to the second chamber so as to enable fluid to outlet directly from the second chamber.

13. The device of claim 12, wherein the inlet port and the outlet port are located, with reference to an operating condition of the collecting device, at a lower height with respect to the passage connecting the first and the second chamber in fluid communication, and wherein said outlet port is located at a lowest position, with reference to an operating condition of the second chamber of the collecting device.

14. The device of claim 13, further comprising:
a protruding part which emerges from a portion of a lateral wall of the rigid container, with reference to an operating configuration in which the lateral wall extends from below in an upwards direction, the protruding part developing inferiorly with respect to the first chamber and in prolongation with respect to the lateral wall, wherein the inlet port is located and connected to the protruding part, and
the outlet port is connected at a vertically lowest zone of said protruding part.

15. The device of claim 13 wherein the auxiliary container comprises:
a rigid wall formed by a portion of the lateral wall of the rigid container and by the protruding part, and
a flexible wall peripherally and sealedly fixed to the rigid wall of the auxiliary container.

16. The device of claim 13, comprising:
a supply channel fixed to the inlet port;
a discharge channel fixed to the outlet port;
a bypass channel having a first end connected to the supply channel and a second end connected to the discharge channel for bypassing the fluid collecting device;
a first intercept organ on the bypass channel;
a second intercept organ on the supply channel in a zone comprised between the inlet port and an end of the bypass channel;
a third intercept organ on the discharge channel in a zone comprised between the outlet port and another end of the bypass channel;
a first connector located on a terminal part of the supply channel opposite the inlet port; and
a second connector located on the discharge channel opposite the outlet port, the first connector and the second connector being configured to enable disengagement of the collecting device relative to a respective line of an extracorporeal circuit.

17. A collecting device of biological fluids for medical use, comprising:
a rigid container internally defining at least a first chamber having a fixed volume;
an auxiliary container having at least a deformable portion internally defining a second chamber having a variable volume according to a position of the deformable portion;
at least an inlet port connected with at least one of the rigid container and the auxiliary container;
at least an exit port connected with at least one of the rigid container and the auxiliary container;
at least a passage being provided for setting the first chamber and the second chamber in fluid communication;
a supply channel connected with the inlet port;
a discharge channel connected with the outlet port;
a bypass channel having a first end connected with the supply channel and a second end connected with the discharge channel for bypassing the fluid collecting device;
a first intercept organ on the bypass channel; and
at least one in the group of: a second intercept organ operating on the supply channel and a third intercept organ on the discharge channel.

18. The device of claim 17, wherein
the auxiliary container comprises a deformable portion that is perimetrally constrained to at least a corresponding portion of a lateral wall of the rigid container, the auxiliary container comprising both the inlet port and the outlet port,
the rigid container is box-shaped and has a bottom wall, the lateral wall emerging from the bottom wall, and a closing portion located at a top of the lateral wall, the bottom wall, the lateral wall, and the closing portion defining the volume of the first chamber, and
at least one ventilation line connects the first chamber and an external environment.

19. The device of claim 17, wherein the rigid container and the auxiliary container are mutually flanked, and wherein a portion of the lateral wall of the rigid container is a separating wall between the first chamber and the second chamber and constitutes a common wall between the rigid container and the auxiliary container.

20. The device of claim 17, wherein the rigid container and the auxiliary container are mutually flanked and the auxiliary container comprises a respective bag fixedly connected with the rigid container.

21. The device of claim 17, further comprising a protruding part emerging from a portion of a lateral wall of the rigid container, with reference to an operating configuration in which the lateral wall extends from below in an upwards direction, the protruding part developing inferiorly with respect to the first chamber and in prolongation with respect to the lateral wall, wherein
   the auxiliary container comprises a rigid wall formed by a portion of the lateral wall of the rigid container and by said protruding part with respect to the first chamber, and a flexible wall peripherally fixed in a sealed manner to the rigid wall of the auxiliary container, and
   the inlet and outlet ports are located, with reference to an operating condition of the device, at a lower height with respect to the passage connecting the first chamber and the second chamber in fluid communication, the inlet port and the outlet port being directly connected to said protruding part.

22. The device of claim 17, wherein
   the passage connecting the first chamber and the second chamber in fluid communication is located at a bottom of the first chamber, and
   a bottom wall of the first chamber is inclined downwards proceeding nearingly to the second chamber, such that outflow of fluid through the passage from the first chamber to the second chamber is facilitated.

23. The device of claim 17, further comprising a fluid intercept element that is manually activatable from outside and operates at the passage, the fluid intercept element being displaceable between a first operating position in which a fluid passage is enabled between the first chamber and the second chamber and a second operating condition in which the fluid passage between the first chamber and the second chamber is prevented.

24. The device of claim 17,
   further comprising the second intercept organ, and the third intercept organ, the first end of the bypass channel being connected upstream of the second intercept organ applied on the supply channel and the second end of the bypass channel being connected downstream of the third intercept organ applied on the discharge channel.

25. A collecting device for biological fluids for medical use, comprising:
   a rigid container exhibiting a box conformation having a bottom wall, a lateral wall emerging from the bottom wall, and a closing portion located at a top of the lateral wall, the bottom wall, the lateral wall, and the closing portion internally defining at least a first chamber having a fixed volume;
   an auxiliary container having at least a deformable portion which is constrained to at least a corresponding portion of the lateral wall of the rigid container, said auxiliary container internally defining a second chamber having a variable volume according to a position of the deformable portion;
   at least a passage able to set the first chamber and the second chamber in fluid communication;
   at least one inlet port connected with at least one of the rigid container and the auxiliary container;
   at least one exit port connected with at least one of the rigid container and the auxiliary container;
   at least one fluid intercept element manually drivable from outside the device and operating at the passage setting the first chamber and the second chamber in fluid communication, the fluid intercept element being displaceable between a first operating position, in which a fluid passage is enabled between the first chamber and the second chamber, and a second operating condition, in which the fluid passage between the first chamber and the second chamber is prevented; wherein
   the fluid intercept element comprises a wall element which is substantially cylindrical and rotatably engaged internally of the passage, and which has at an axial end thereof a fluid passage opening set in communication with the second chamber and further having a fluid passage opening made at a lateral wall of the cylindrical surface; following an angular rotation of the fluid intercept element, the opening located on the cylindrical wall being displaceable between a condition in which the opening opens towards the first chamber and sets the first chamber in fluid communication with the second chamber, and a second angularly offset position with respect to the first position in which the opening located on the cylindrical lateral wall is closed by a corresponding part of the passage, in this way preventing fluid communication between the first chamber and the second chamber.

26. The device of claim 25, wherein the passage connecting the first and the second chambers in fluid communication is located at a bottom of the first chamber.

27. A collecting device for biological fluids for medical use, comprising:
   a rigid container exhibiting a box conformation having a bottom wall, a lateral wall emerging from the bottom wall, and a closing portion located at a top of the lateral wall, the bottom wall, the lateral wall, and the closing portion internally defining at least a first chamber having a fixed volume;
   an auxiliary container having at least a deformable portion which is constrained to at least a corresponding portion of the lateral wall of the rigid container, said auxiliary container internally defining a second chamber having a variable volume according to a position of the deformable portion;
   at least a passage able to set the first chamber and the second chamber in fluid communication;
   at least one inlet port connected with at least one of the rigid container and the auxiliary container; and
   at least one exit port connected with at least one of the rigid container and the auxiliary container, wherein
   the inlet port is directly connected to the second chamber so as to enable inlet directly to the second chamber,
   the outlet port directly connected to the second chamber so as to enable outlet directly from the second chamber, and
   the inlet port and the outlet port are located, with reference to an operating condition of the collecting device, at a lower height with respect to the passage connecting the first chamber and the second chamber in fluid communication.

28. The device of claim 27, wherein the auxiliary container deformable portion comprises at least one deformable wall peripherally constrained to the lateral wall of the rigid container, wherein
   the rigid container and the auxiliary container are mutually flanked, and
   a portion of the lateral wall of the rigid container separates the first chamber and the second chamber and constitutes a portion of wall in common between the rigid container and the auxiliary container.

29. The device of claim 28, wherein
a protruding part emerges from a portion of lateral wall of the rigid container, with reference to an operating configuration in which the lateral wall extends from below in an upwards direction, the protruding part developing inferiorly with respect to the first chamber and in prolongation with respect to the lateral wall, and
the auxiliary container comprises:
a rigid wall formed by a portion of the lateral wall of the rigid container and by the protruding part, and
a flexible wall peripherally and sealedly fixed to the rigid wall of the auxiliary container, and
wherein the inlet port is located and connected to the protruding part and the outlet port is connected at a vertically lowest zone of said protruding part.

30. A collecting device for biological fluids for medical use, comprising:
a rigid container exhibiting a box conformation having a bottom wall, a lateral wall emerging from the bottom wall, and a closing portion located at a top of the lateral wall, the bottom wall, the lateral wall, and the closing portion internally defining at least a first chamber having a fixed volume;
an auxiliary container having at least a deformable portion which is constrained to at least a corresponding portion of the lateral wall of the rigid container, said auxiliary container internally defining a second chamber having a variable volume according to a position of the deformable portion;
at least a passage able to set the first chamber and the second chamber in fluid communication;
at least one inlet port connected with at least one of the rigid container and the auxiliary container;
at least one exit port connected with at least one of the rigid container and the auxiliary container;
a supply channel fixed to the inlet port;
a discharge channel fixed to the outlet port;
a bypass channel having a first end connected to the supply channel and a second end connected to the discharge channel for bypassing the fluid collecting device;
a first intercept organ on the bypass channel;
a second intercept organ on the supply channel in a zone comprised between the inlet port and an end of the bypass channel;
a third intercept organ on the discharge channel in a zone comprised between the outlet port and another end of the bypass channel;
a first connector located on a terminal part of the supply channel opposite the inlet port; and
a second connector located on the discharge channel opposite the outlet port, the first connector and the second connector being configured for enabling disengagement of the collecting device relative to a respective line of an extracorporeal circuit.

31. A collecting device for biological fluids for medical use, comprising:
a rigid container exhibiting a box conformation having a bottom wall, a lateral wall emerging from the bottom wall, and a closing portion located at a top of the lateral wall, the bottom wall, the lateral wall, and the closing portion internally defining at least a first chamber having a fixed volume;
an auxiliary container having at least a deformable portion which is constrained to at least a corresponding portion of the lateral wall of the rigid container, said auxiliary container internally defining a second chamber having a variable volume according to a position of the deformable portion;
at least a passage able to set the first chamber and the second chamber in fluid communication;
at least one inlet port connected with at least one of the rigid container and the auxiliary container;
at least one exit port connected with at least one of the rigid container and the auxiliary container; and
at least a housing connected upstream of the inlet port and internally comprising at least a hydrophilic membrane configured to (i) enable passage of fluid from a first section upstream of the housing towards a second section downstream thereof, (ii) reduce passage of air, the membrane being arranged internally of the housing, and (iii) separate the housing into an upstream half-chamber and a downstream half-chamber, a passage for gas evacuation being provided at the upstream half-chamber.

* * * * *